(12) United States Patent
Hacikyan et al.

(10) Patent No.: US 12,228,543 B2
(45) Date of Patent: Feb. 18, 2025

(54) HANDHELD PORTABLE OXYGEN MONITOR

(71) Applicant: Aquasol Corporation, LLC, North Tonawanda, NY (US)

(72) Inventors: Michael Hacikyan, Naples, FL (US); Vamshi Krishna Eranki, Buffalo, NY (US); Srinivas Reddy Adulla, Buffalo, NY (US)

(73) Assignee: AQUASOL CORPORATION, LLC, North Tonawanda, NY (US)

( * ) Notice: Subject to any disclaimer, the term of this patent is extended or adjusted under 35 U.S.C. 154(b) by 530 days.

(21) Appl. No.: 17/303,058

(22) Filed: May 19, 2021

(65) Prior Publication Data

US 2022/0373501 A1 Nov. 24, 2022

(51) Int. Cl.
  *G01N 27/409* (2006.01)
  *B23K 9/32* (2006.01)
  (Continued)

(52) U.S. Cl.
  CPC ............. *G01N 27/409* (2013.01); *B23K 9/32* (2013.01); *G01N 1/2205* (2013.01);
  (Continued)

(58) Field of Classification Search
  CPC .... G01N 27/409; G01N 27/4065; G01N 1/24; G01N 1/4077; G01N 2001/4088; G01N 27/407; G01N 27/4073
  See application file for complete search history.

(56) References Cited

U.S. PATENT DOCUMENTS

| 5,187,343 A | 2/1993 | Edwards |
| 5,479,359 A | 12/1995 | Rogero et al. |

(Continued)

FOREIGN PATENT DOCUMENTS

| CN | 201689072 U | 12/2010 |
| CN | 105006666 B | 6/2018 |

(Continued)

OTHER PUBLICATIONS

Sintered Mesh Filter Element for Precise Filtration (2024) (Year: 2024).*

(Continued)

*Primary Examiner* — Brian W Cohen
*Assistant Examiner* — Vivian A Tran
(74) *Attorney, Agent, or Firm* — Walter W. Duft

(57) ABSTRACT

A handheld portable oxygen monitor for monitoring oxygen includes one or more of (1) a replaceable dust filter element removably disposed in a gas inlet pathway extending from an gas inlet port to an oxygen sensor, (2) an oxygen sensor module including the oxygen sensor and a circuit board on which the oxygen sensor is mounted, the oxygen sensor module being removably mounted to a circuit board holder, (3) configurable gas pathway components within the oxygen monitor housing, and (4) a controller operable to enable a remote device to (a) control one or more operations of the oxygen monitor, (b) receive real-time oxygen monitoring data from the oxygen monitor for display on the remote device, (c) upload logging event data from the oxygen monitor storage, (d) obtain system information from the oxygen monitor storage, and (e) perform firmware updates on the oxygen monitor to modify its programming.

18 Claims, 13 Drawing Sheets

(51) Int. Cl.
*G01N 1/22* (2006.01)
*G01N 1/40* (2006.01)
*G01N 27/406* (2006.01)
*G01N 27/407* (2006.01)

(52) U.S. Cl.
CPC ......... *G01N 1/2273* (2013.01); *G01N 1/4077* (2013.01); *G01N 27/4065* (2013.01); *G01N 27/407* (2013.01); *G01N 2001/4088* (2013.01)

(56) References Cited

U.S. PATENT DOCUMENTS

| | | |
|---|---|---|
| 6,167,766 B1 | 1/2001 | Dunn et al. |
| 9,829,472 B2 | 11/2017 | Hacikyan |
| 10,371,679 B2 | 8/2019 | Hacikyan |
| 2002/0009119 A1 | 1/2002 | Matthew et al. |
| 2002/0178789 A1* | 12/2002 | Sunshine ........... G01N 33/0009 73/31.06 |
| 2003/0138329 A1* | 7/2003 | Koyano ................ G08B 21/14 417/63 |
| 2003/0173205 A1 | 9/2003 | Karlsson et al. |
| 2004/0062684 A1 | 4/2004 | McGee |
| 2007/0035255 A1 | 2/2007 | Shuster et al. |
| 2007/0107594 A1 | 3/2007 | Piccinni et al. |
| 2012/0191349 A1 | 7/2012 | Lenz et al. |
| 2013/0244336 A1 | 9/2013 | Mayer et al. |
| 2014/0102175 A1 | 4/2014 | Wasden |
| 2014/0284222 A1 | 9/2014 | Wanek, Jr. et al. |
| 2015/0076129 A1 | 3/2015 | Spear |
| 2015/0273607 A1 | 10/2015 | Denis et al. |
| 2016/0061799 A1 | 3/2016 | Epperson |
| 2016/0069833 A1 | 3/2016 | Hacikyan |
| 2016/0101481 A1 | 4/2016 | Holverson et al. |
| 2016/0221107 A1 | 8/2016 | Kadlec |
| 2018/0128799 A1* | 5/2018 | Hacikyan ........... G01N 33/0075 |
| 2023/0314391 A1* | 10/2023 | Millar ................ G01N 33/0022 422/98 |

FOREIGN PATENT DOCUMENTS

| | | |
|---|---|---|
| EP | 059529 B1 | 8/1998 |
| GB | 2457053 A | 8/2009 |
| JP | 2016024797 A * | 2/2016 |
| WO | WO2016153562 A1 | 9/2016 |

OTHER PUBLICATIONS

Boettinger et al., 7—Solidification, Physical Metallurgy, Fifth Edition, pp. 639-850 (2014) (Year: 2014).*
Oyishi et al., An Overview of the State of the Art and Applications of Sintered Metals, IOSR Journal of Mechanical and Civil Engineering, vol. 17, Issue 4, pp. 1-10 (2020) (Year: 2020).*
Neutronics Inc., "Model OA-1S+ Portable Ultra-Trace Oxygen Analyzer Operations Manual", Oct. 2004, 29 pages.
Neutronics Inc., "Model N2 Operations Manual", Oct. 2006, 28 pages.
Neutronics Inc., "Model 7100P Portable Oxygen Analyzer—Trace Range Operations Manual", Jan. 2001, 58 pages.
Huntingdon Fusion Techniques, "Argweld Purgeye 300 Weld Purge Monitor", Sep. 2013, 2 pages.
Huntingdon Fusion Techniques, "Argweld Purgeye 500 Weld Purge Monitor", Sep. 2013, 2 pages.
Huntingdon Fusion Techniques, "Purgeye 600 Weld Purge Monitor", Sep. 2013, 2 pages.
Huntingdon Fusion Techniques, "Purgeye 100 Weld Purge Monitor", May 2013, 4 pages.
Prestige Industrial Pipework Equipment, "Handy Purge Pro 5", Dec. 2011, 1 page.
Prestige Industrial Pipework Equipment, "Pro Purge 1 Weld Purge Monitor", Apr. 2014, 1 page.
TVC LTD, "ALX II Portable Arc Welding Data-Logger and Monitoring System", May 2013, 2 pages.
TVC LTD, "ALX II RS Arc Welding Data-Logger and Monitoring System", Nov. 2010, 2 pages.
Advanced Instruments Inc., "GPR-1200 MS Portable ppm Oxygen Analyzer", Oct. 2009, 32 pages.
KIPO, PCT International Search Report, PCT International Application No. PCT/2022/071914 entitled "Handheld Portable Oxygen Monitor", Aug. 17, 2022, 4 pages.
KIPO, Written Opinion of the International Searching Authority, PCT International Application No. PCT/2022/071914 entitled "Handheld Portable Oxygen Monitor", Aug. 17, 2022, 8 pages.

* cited by examiner

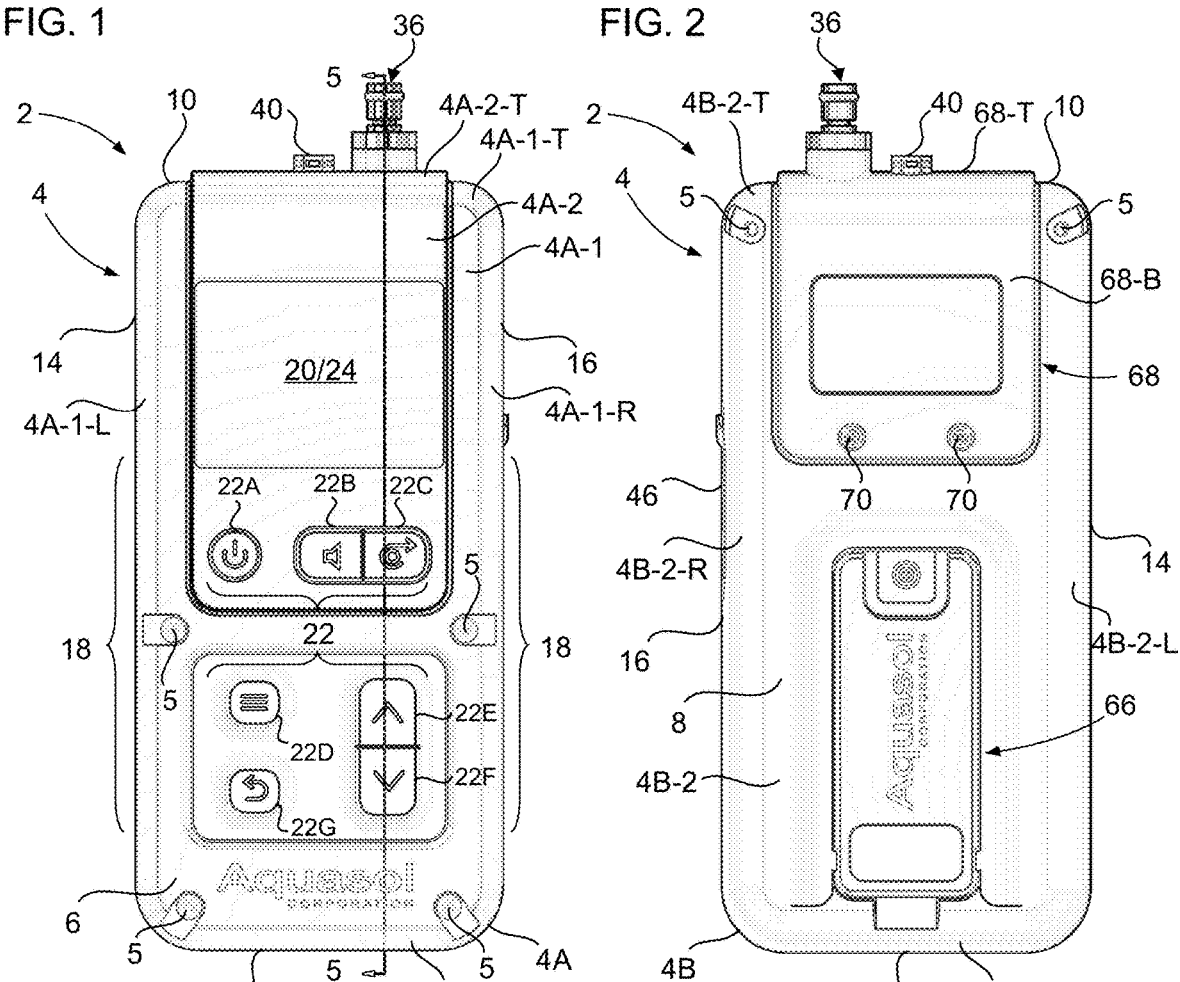

FIG. 5
FIG. 6
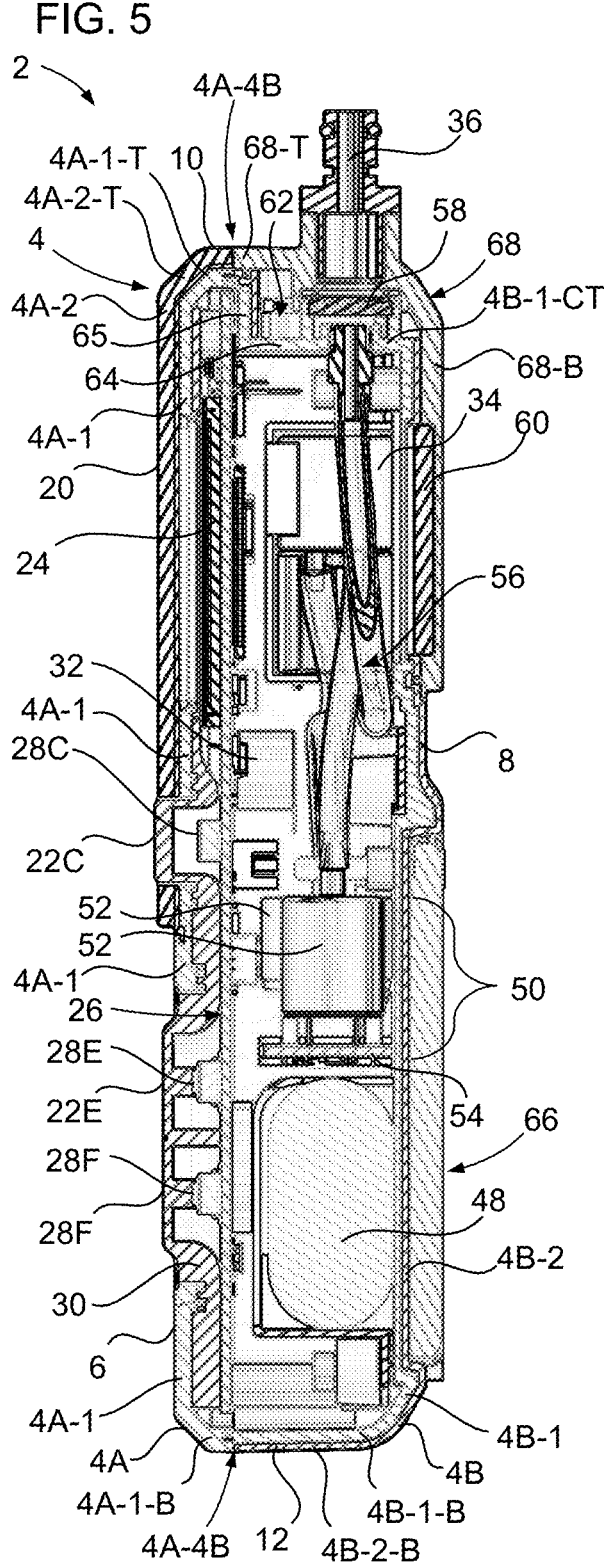
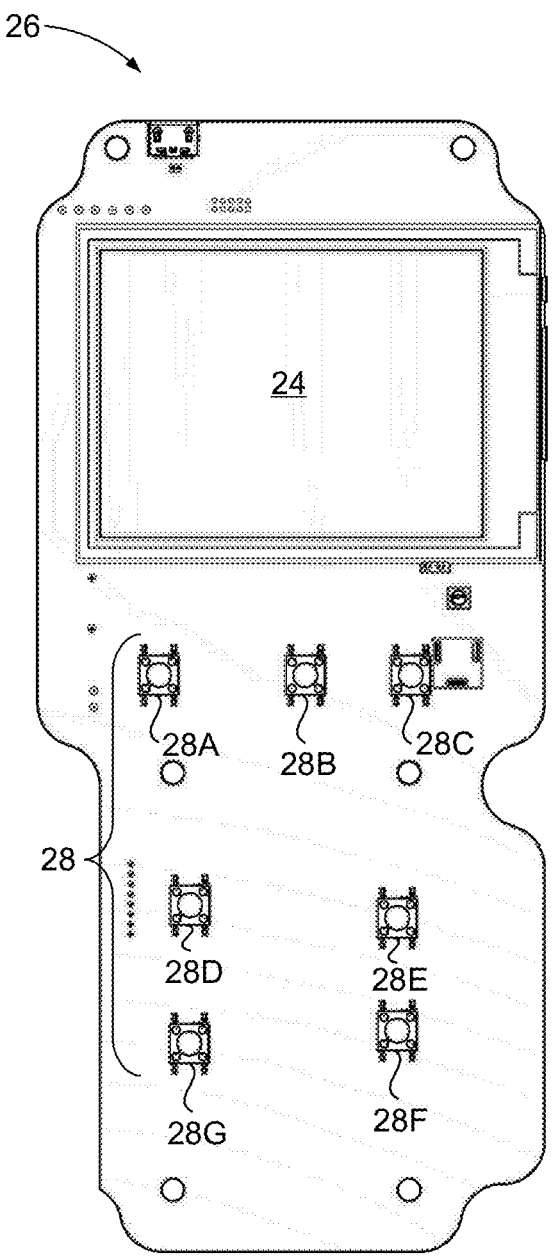

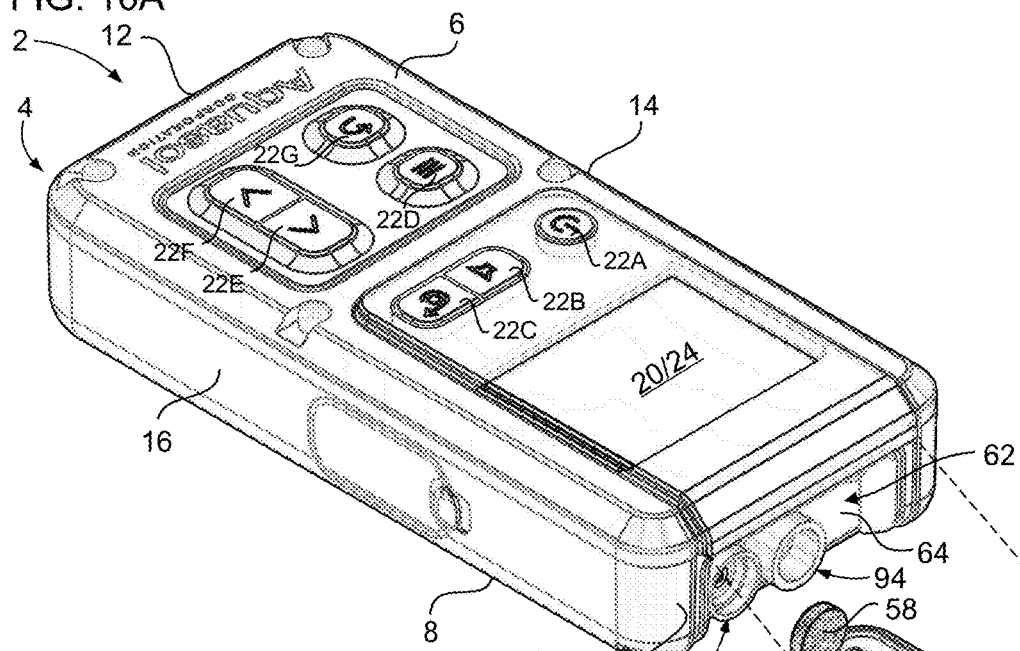
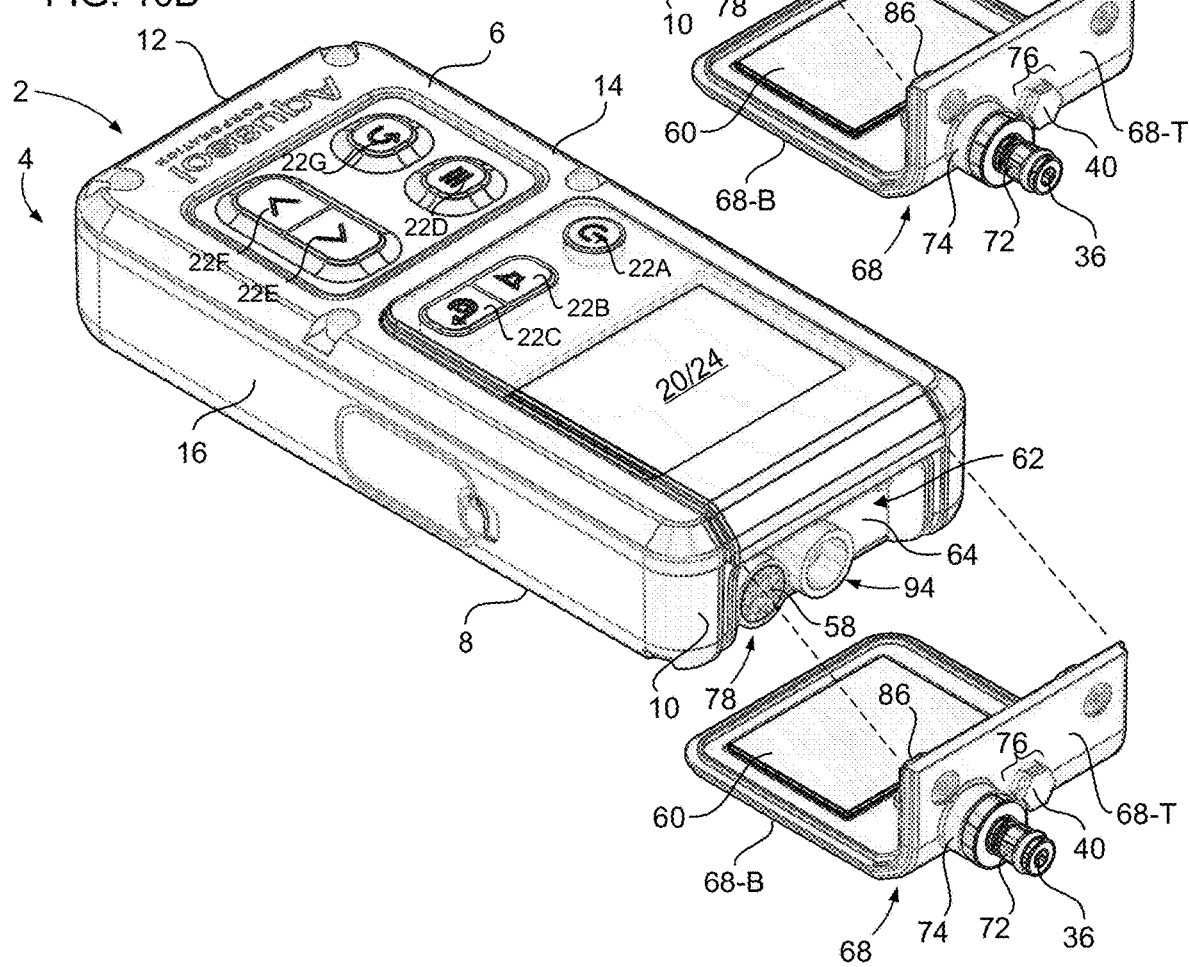

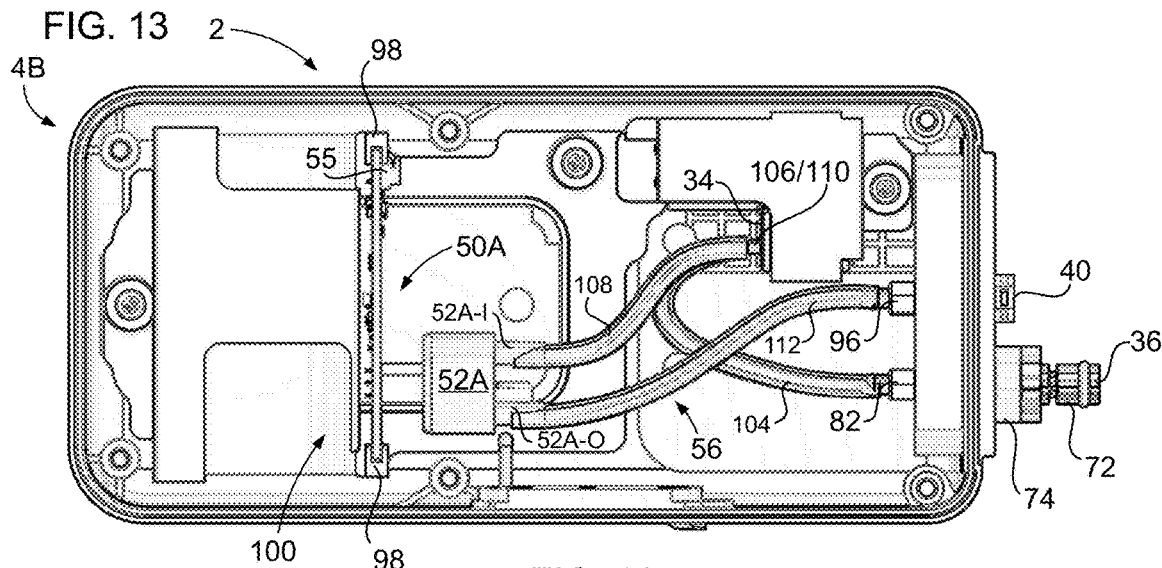
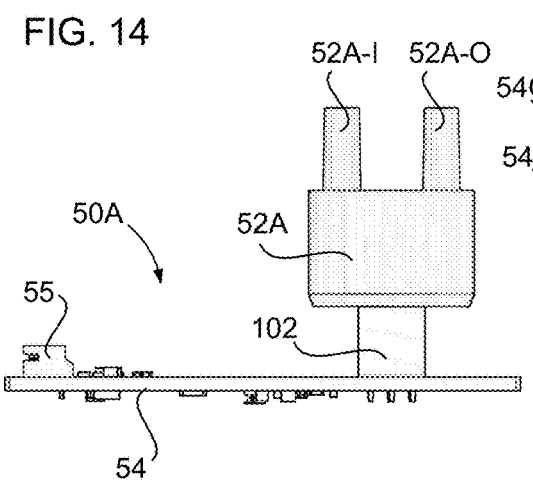
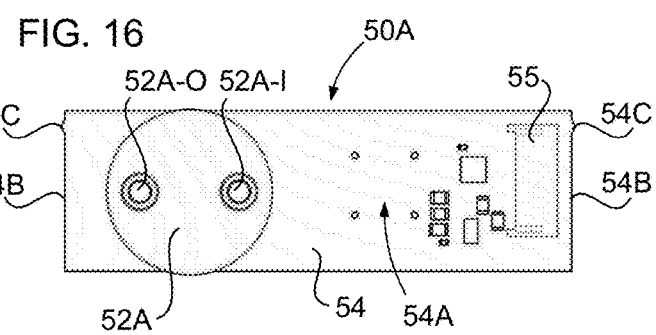
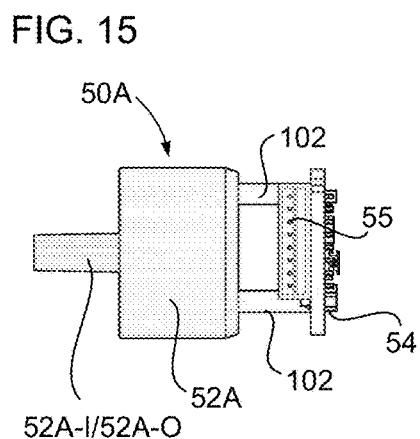
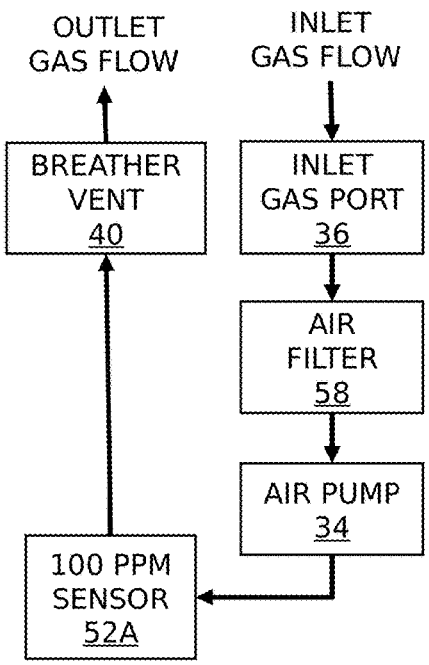

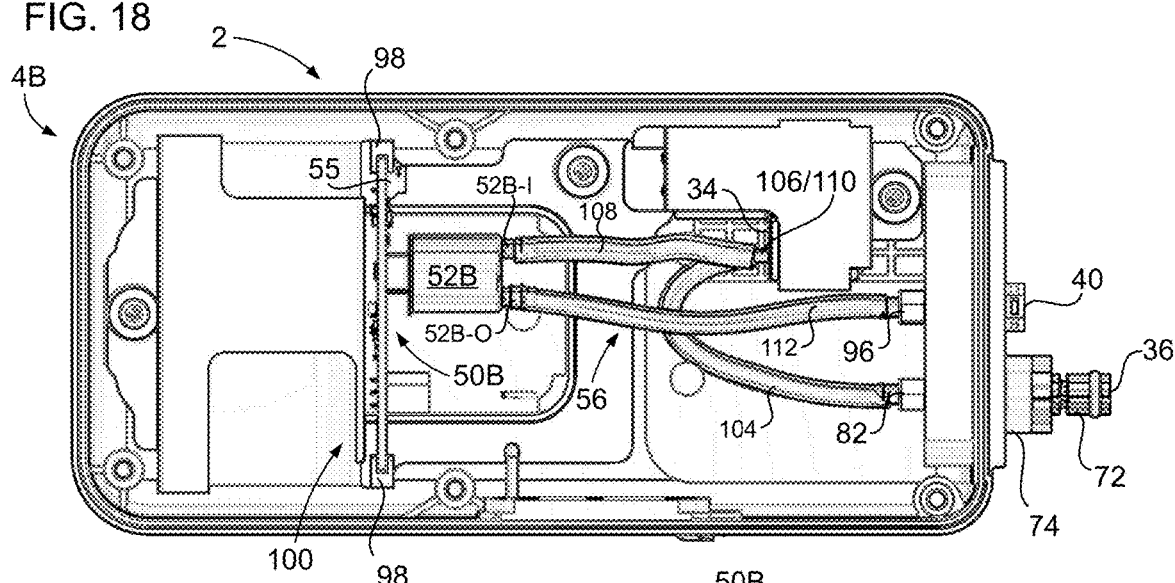
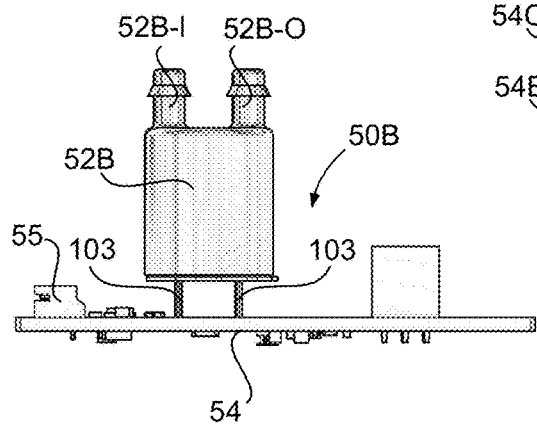
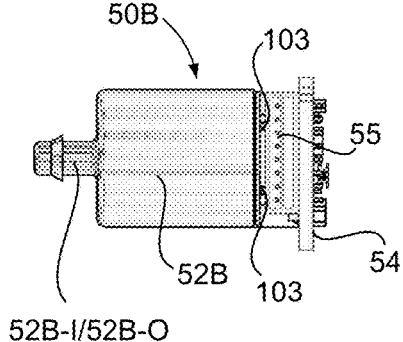
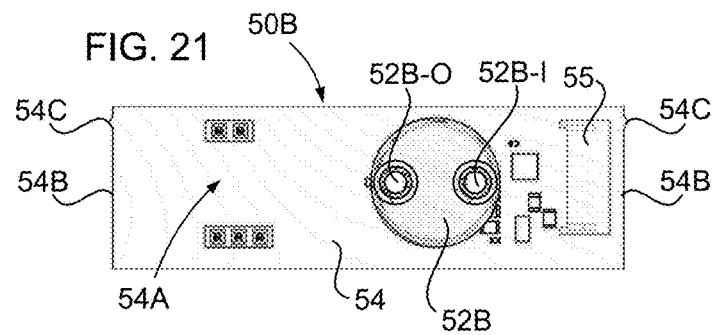
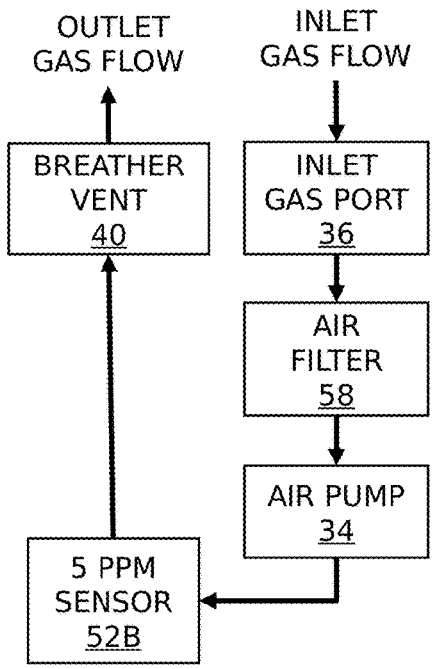

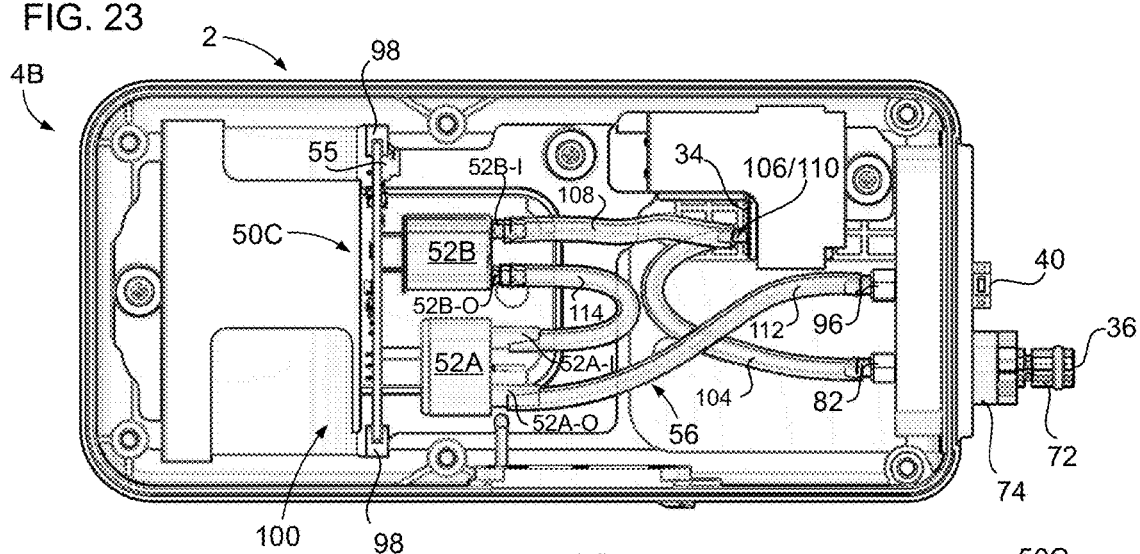
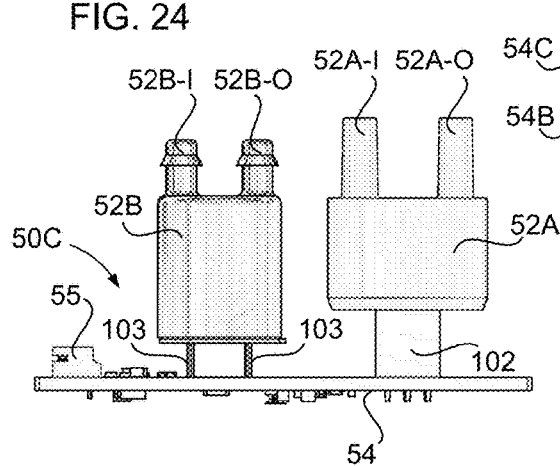
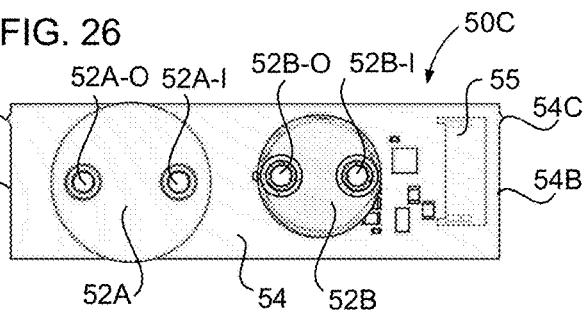
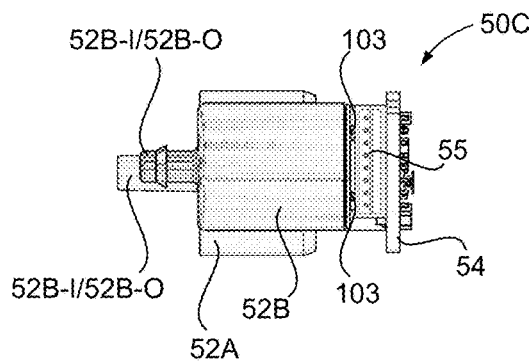
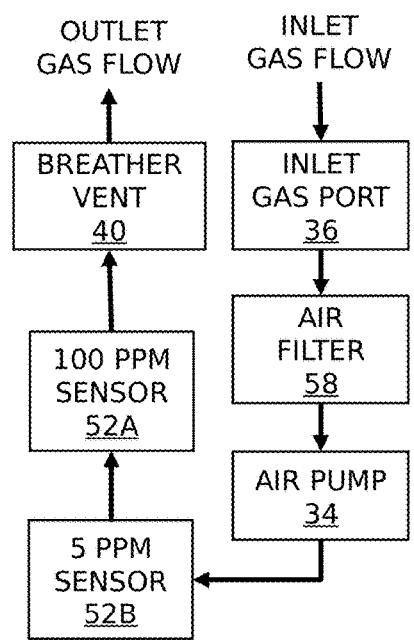

FIG. 29A
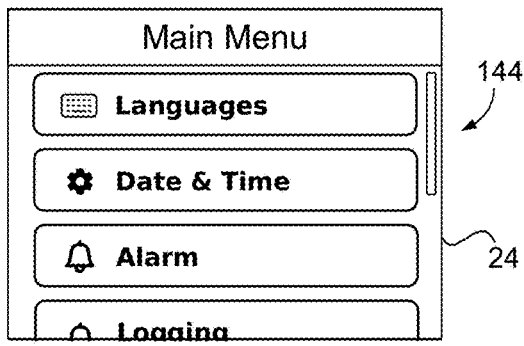
FIG. 30A
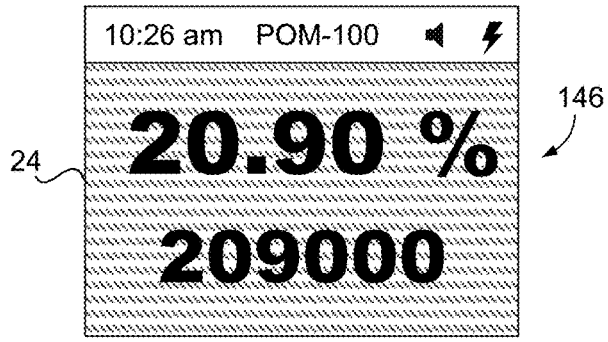
FIG. 29B
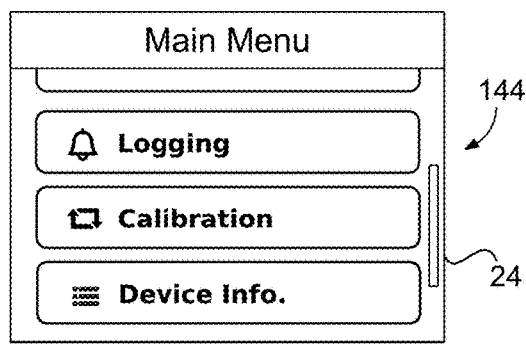
FIG. 30B
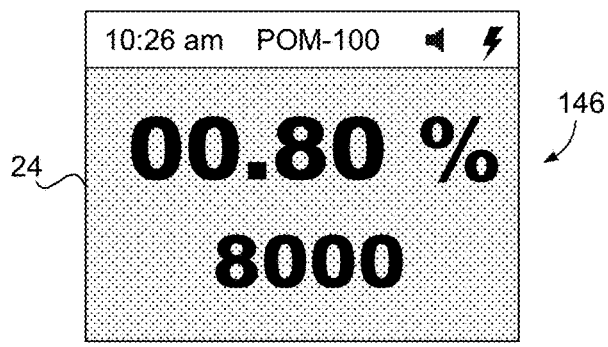
FIG. 29B-1
| Device Info. | |
|---|---|
| Model | POM-100 |
| HI CAL | 20/04/21, 10:00:00, 208500 |
| LO CAL | 20/04/21, 10:15:00, 500 |
| S NO | 106046 |
| SEN NO | 0024843792 |
FIG. 30C
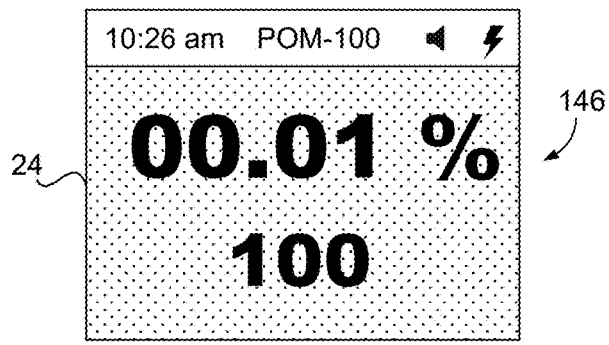
FIG. 31
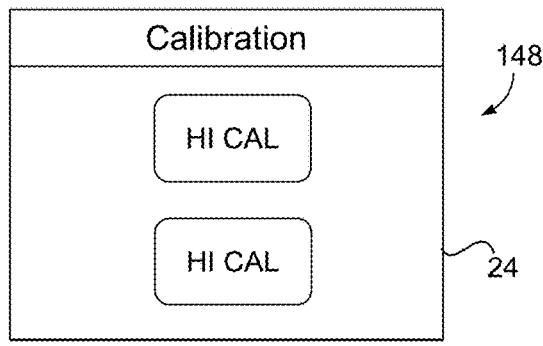

HANDHELD PORTABLE OXYGEN MONITOR

BACKGROUND

1. Field

The present disclosure relates generally to inert gas welding. More particularly, the invention is directed to oxygen monitors for monitoring oxygen around a weld zone prior to and during an inert gas welding operation.

2. Description of the Prior Art

By way of background, inert gas welding is a species of arc welding in which the molten weld pool is shielded from atmospheric contamination and oxidation by bathing it with an inert gas, such as Argon, or a mixture of Helium and Argon. Popular examples of inert gas welding include TIG (Tungsten Inert Gas) welding and MIG (Metal Inert Gas) welding.

When welding together pipes and other enclosed structures using inert gas welding, it is important to purge the interior of the pipe or structure in the vicinity of the weld zone to prevent corrosion and the formation of oxides on the interior side of the weld pool. Purge dams are conventionally used for this purpose. For example, when butt-welding the ends of two pipe sections to form a consolidated pipe run, two purge dam structures are placed in the pipes, one in each pipe end on either side of the weld zone. A purge gas can then be introduced into the area between the dams to displace the oxygen therein.

It is common to use an oxygen monitor to determine whether sufficient oxygen removal has taken place for welding operations to proceed. Historically, such oxygen monitors have been non-portable apparatus of relative large size. More recently, portable oxygen monitors that are hand-held and battery powered have become available. Although the portability of such devices enhances ease of use, hand-held oxygen monitors typically lack one or more features, which limits their usability in the field.

It is to improvements in the design and operation of portable oxygen monitors that the present disclosure is directed.

SUMMARY

A handheld portable oxygen monitor for monitoring oxygen in a weld zone is provided. The oxygen monitor includes an oxygen monitor housing having a front, a back, a top, a bottom, and two sides extending between the front and back and the top and bottom. The housing has a hand-holding portion that is sized and configured to be held in the palm of a hand of a monitor user, with the user's thumb engaging one of the sides and the user's remaining fingers engaging the other of the sides. A user interface is provided on the front of the housing. The user interface includes an oxygen monitor display and one or more user interface buttons. A gas inlet port is configured to receive a gas. An oxygen sensor is operable to receive the gas from the gas inlet port, detect oxygen in the gas, and generate oxygen sensor outputs indicative of oxygen levels in the gas. A pump has a pump inlet in fluid communication with the inlet gas port and a pump outlet in fluid communication with the oxygen sensor. The oxygen monitor further includes one or more additional components selected from the group consisting of:

(1) a replaceable dust filter element removably disposed in a gas inlet pathway extending from an gas inlet port to an oxygen sensor;
(2) an oxygen sensor module including the oxygen sensor and a circuit board on which the oxygen sensor is mounted, the oxygen sensor module being removably mounted to a circuit board holder;
(3) configurable gas pathway components within the oxygen monitor housing; and
(4) a controller operable to enable a remote device to (a) control one or more operations of the oxygen monitor, (b) receive real-time oxygen monitoring data from the oxygen monitor for display on the remote device, (c) upload logging event data from the oxygen monitor storage, (d) obtain system information from the oxygen monitor storage, and (e) perform firmware updates on the oxygen monitor to modify its programming.

In another aspect, a handheld portable oxygen monitor as summarized above is provided in combination with a remote device that is operable to (a) control one or more operations of the oxygen monitor, (b) receive and display real-time oxygen monitoring data from the oxygen monitor, (c) upload logging event data from the oxygen monitor storage, (d) obtain system information from the oxygen monitor storage, and (e) perform firmware updates on the oxygen monitor to modify its programming. In an embodiment, the remote device may be further operable to communicate oxygen monitor information obtained from the oxygen monitor to a second remote device for manufacturer analysis of oxygen monitor operations.

BRIEF DESCRIPTION OF THE DRAWINGS

The foregoing and other features and advantages will be apparent from the following more particular description of example embodiments, as illustrated in the accompanying Drawings.

FIG. 1 is a front plan view showing a handheld portable oxygen monitor that may be constructed in accordance with the present disclosure.

FIG. 2 is a rear plan view of the oxygen monitor of FIG. 1.

FIG. 3 is a left side elevation view of the oxygen monitor of FIG. 1.

FIG. 4 is a right side elevation view of the oxygen monitor of FIG. 1.

FIG. 5 is a cross-sectional view taken along line 5-5 in FIG. 1.

FIG. 6 is a plan view of a main circuit board of the oxygen monitor of FIG. 1.

FIG. 10A is a perspective view of the oxygen monitor of FIG. 1, with a removable cover of the oxygen monitor being detached therefrom to illustrate a removable dust filter element of the oxygen monitor being installed or removed.

FIG. 10B is a perspective view of the oxygen monitor of FIG. 1, with a removable cover of the oxygen monitor being detached therefrom to illustrate a removable dust filter element seated in a filter receptacle.

FIG. 13 is a plan view of the oxygen monitor of FIG. 1, with a top cover portion thereof removed to illustrate a bottom cover portion and components therein, the components including a first removable oxygen sensor module that may be installed in the oxygen monitor and corresponding configurable gas pathway components.

FIG. 14 is a top edge view of the first removable oxygen sensor module of FIG. 13.

FIG. 15 is an end view of the first removable oxygen sensor module of FIG. 13.

FIG. 16 is a plan view of the first removable oxygen sensor module of FIG. 13.

FIG. 17 is a functional block diagram illustrating gas flow to and from the first removable oxygen sensor module of FIG. 13.

FIG. 18 is a plan view of the oxygen monitor of FIG. 1, with a top cover portion thereof removed to illustrate a bottom cover portion and components therein, the components including a second removable oxygen sensor module that may be installed in the oxygen monitor.

FIG. 19 is a top edge view of the second removable oxygen sensor module of FIG. 18.

FIG. 20 is an end view of the second removable oxygen sensor module of FIG. 18.

FIG. 21 is a plan view of the second alternative oxygen sensor module of FIG. 18.

FIG. 22 is a functional block diagram illustrating gas flow to and from the second removable oxygen sensor module of FIG. 18.

FIG. 23 is a plan view of the oxygen monitor of FIG. 1, with a top cover portion thereof removed to illustrate a bottom cover portion and components therein, the components including a third removable oxygen sensor module that may be installed in the oxygen monitor.

FIG. 24 is a top edge view of the third removable oxygen sensor module of FIG. 23.

FIG. 25 is an end view of the third removable oxygen sensor module of FIG. 23.

FIG. 26 is a plan view of the third alternative oxygen sensor module of FIG. 23.

FIG. 27 is a functional block diagram illustrating gas flow to and from the second removable oxygen sensor module of FIG. 23.

FIG. 29A is a diagrammatic illustration showing a display of the oxygen monitor of FIG. 1 while displaying a first portion of an options menu.

FIG. 29B is a diagrammatic illustration showing a display of the oxygen monitor of FIG. 1 while displaying a second portion of an options menu.

FIG. 29B-1 is a diagrammatic illustration showing a display of the oxygen monitor of FIG. 1 while displaying device information.

FIG. 30A is a diagrammatic illustration showing a display of the oxygen monitor of FIG. 1 during an initial stage of oxygen monitoring.

FIG. 30B is a diagrammatic illustration showing a display of the oxygen monitor of FIG. 1 during an intermediate stage of oxygen monitoring.

FIG. 30C is a diagrammatic illustration showing a display of the oxygen monitor of FIG. 1 during a final stage of oxygen monitoring.

FIG. 31 is a diagrammatic illustration showing a display of the oxygen monitor of FIG. 1 while displaying a calibration option sub-menu.

DETAILED DESCRIPTION OF EXAMPLE EMBODIMENTS

Figure 7:
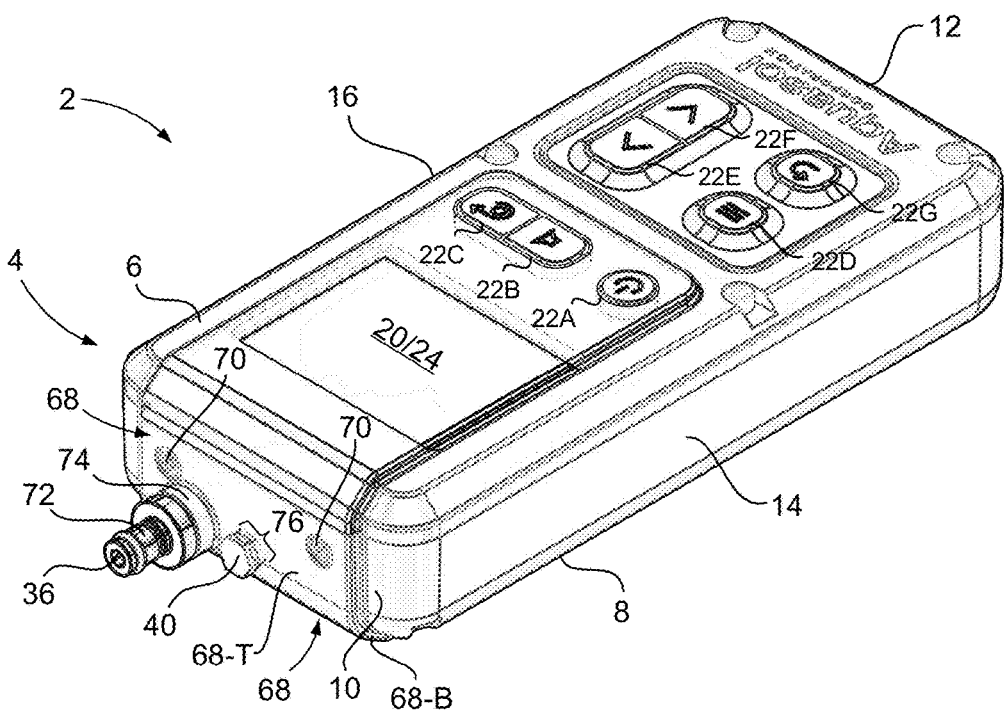
FIG. 7 is a perspective view of the oxygen monitor of FIG. 1.

Turning now to the drawing figures, which are not necessarily to scale, like reference numbers are used to represent like elements in all of the several views. FIGS. 1-4 illustrate a wireless oxygen monitor 2 representing an example oxygen monitor embodiment that may be constructed in accordance with the present disclosure. In the illustrated embodiment, the oxygen monitor 2 is implemented as a portable handheld device particularly suited for in-the-field use. For such applications, it may be necessary to monitor oxygen in a weld zone prior to and during a welding operation performed at a remote location (e.g., as opposed to in a welding shop).

The oxygen monitor 2 includes a monitor housing 4 having a front 6, a back 8, a top 10, a bottom 12, and two sides 14 and 16 extending between the front and back and the top and bottom. Reference numeral 18 in FIG. 1 illustrates the general location of a hand-holding portion of the housing 4. The hand-holding portion 18 is sized and configured to be held in the palm of a monitor user's hand, with the user's thumb engaging one of the two sides (14 or 16) and the user's remaining fingers engaging the other of the two sides (14 or 16). Although the housing is shown as being substantially rectangular with substantially mutually parallel sides and edges, tapered housing configurations could also be used. Regardless, the hand-holding portion 18 of the housing 4 has an average thickness dimension representing the average distance between the front 6 and back 8 of the housing 4 over the length of the hand-holding portion. The hand-holding portion 18 also has an average width dimension representing the average distance between the two sides 14 and 16 of the housing 4 over the length of the hand-holding portion 18. In an example embodiment, the average thickness dimension is preferably less than or equal to the average width dimension to provide satisfactory ergonomic comfort. By way of example, the average thickness dimension may be approximately 1.5-2.5 inches, and the average width dimension may be approximately 2.5-3.5 inches.

FIG. 1 depicts a user interface on the front of the housing 4 that includes a transparent display window 20 and a set of user interface buttons 22. With additional reference now to FIGS. 5 and 6, the display window 20 allows viewing of an underlying alphanumeric display 24 disposed on a main circuit board 26 mounted within the housing 4. By way of example only, the alphanumeric display 24 may comprise a backlit color LCD (liquid crystal display) element. Using a backlit LCD element allows the displayed information to be easily discerned in outdoor sunlit conditions. As also shown in FIGS. 5 and 6, the user interface buttons 22 engage corresponding push-button switches 28 on the main circuit board 26. Alternatively, the user interface buttons 22 and switches 28 could be implemented as touch components on a touch screen (not shown) that could also function as the display 24).

Returning now to FIG. 1, the one or more user interface buttons 22 may include a power button 22A, a speaker button 22B, pump activation button 22C, a menu button 22D, a menu-up scroll button 22E, a menu-down scroll button 22F, and a menu-back button 22G. As can be seen in FIG. 5, the user interface buttons 22A-22G may be formed from a single sheet member 30 made from silicone rubber or other flexible resilient material that is molded or otherwise formed with a surface relief pattern to define raised projections that represent the various user interface buttons. In FIG. 5, which is a cross-sectional view taken along line 5-5 in FIG. 1, the raised projections that form the pump activation button 22C, the menu-up scroll button 22E, and the menu-down scroll button 22D are shown.

The power button 22A (FIG. 1) actuates an underlying power switch 28A (FIG. 6) on the circuit board 26 in order to power-on and power-off the oxygen monitor 2.

The speaker button 22B (FIG. 1) actuates an underlying speaker switch 28B (FIG. 6) on the circuit board 26 in order to mute or unmute an audio sound-generator device 32 (FIG. 5).

The pump button 22C (FIGS. 1 and 5) actuates an underlying pump switch 28C (FIG. 6) on the circuit board 26. Pushing the pump button 22C activates an oxygen monitor air pump 34 (FIG. 5) and initiates an oxygen monitoring mode of the oxygen monitor 2. Pushing the pump button 22C again deactivates the air pump 34 and terminates the oxygen monitoring mode. The oxygen monitoring mode of the oxygen monitor 2 is described in more detail below.

The menu button 22D (FIG. 1) actuates an underlying menu switch 28D (FIG. 6) on the circuit board 26. Pushing the menu button 22D a first time invokes a menu of the oxygen monitor 2 in which a list of menu options are presented on the display 24. Example menu options that may be offered by the oxygen monitor 2 are described in more detail below. Pushing the menu button 22D a second time (and thereafter while the menu is active) selects a highlighted one of the menu options. The menu options may be hierarchically organized into sub-menus.

The menu-up and menu-down scroll buttons 22E and 22F respectively actuate underlying menu-up and menu-down switches 28E and 28F (FIG. 6) on the circuit board 26. The menu-up scroll button 22E navigates through the menu options presented on the display 24 in an upward scrolling direction. The menu-down scroll button 22F navigates through the menu options in a downward scrolling direction. Individual menu options are successively highlighted as scrolling proceeds in either direction. As noted above, after scrolling to a desired menu option, the highlighted option may be selected by pushing the menu button 22D.

The menu-back button 22G (FIG. 1) actuates an underlying menu-back switch 28G (FIG. 6) on the circuit board 26. If the menu options of the oxygen monitor 2 are arranged hierarchically, pushing the menu-back button 22G will exit the current menu or sub-menu and return to the next higher level in the menu hierarchy. Exiting from the top-level menu of the menu hierarchy terminates the menu display of the oxygen monitor 2. Exiting from a sub-menu returns to the next higher level in the menu hierarchy. If the menu is not hierarchical, pushing the menu-back button 22G will always terminate the menu display.

As shown in FIGS. 1-5, the oxygen monitor 2 further includes a gas inlet port 36 that may be situated at the top 10 of the housing 4. The gas inlet port 36 is operable to connect the oxygen monitor 2 to a gas sampling probe 38 (shown in FIG. 32) that delivers a gas to be sampled by the oxygen monitor 2. An apertured breather vent 40 (shown in FIGS. 1-3) may also be disposed at the top 10 of the housing 4 in order to vent the sampled gas to atmosphere following sampling.

As can be seen in FIG. 4, a digital wireline communication port 42 and a charge port 44 may be provided on the right side 16 of the housing 4. The wireline communication port 42 is operable to connect the oxygen monitor to a remote computing device via a suitable data cable. The charge port 44 is operable to connect the oxygen monitor 2 to a charging device or other external power source (such as the charger 130 shown in FIG. 28). Both of the ports 42 and 44 may be implemented with any suitable type of connector, including but not limited to a universal serial bus (USB) connector. Note that the illustrated embodiment of FIG. 4 depicts the digital wireline communication port 42 and the charge port 44 using hidden-line representation because these components are situated beneath a hinged flap 46 that protects the communication and charge ports from environmental contaminants. The hinged flap 46 (which is also visible in FIG. 2) may formed from silicon rubber or other suitable material.

As shown near the bottom of FIG. 5, the oxygen monitor further includes a direct current internal power source 48 that is operable via the power button/power switch 22A/28A. The power source 48 is connected to provide electrical power to various oxygen monitor components, and to receive electrical power from the charge port 44. In an example embodiment, the power source 48 may be implemented as a rechargeable battery.

As shown near the mid-point of FIG. 5, an oxygen sensor module 50 may be disposed within the housing 4 to provide a modular sensor system. The oxygen sensor module 50 may include one or more oxygen sensors 52 (two are shown) mounted on an oxygen sensor circuit board 54 that may be designed so as to be readily removable from the oxygen monitor 2 for repair or replacement. Additional features of the oxygen sensor module 50 are described in more detail below. As also described in more detail below, configurable internal gas pathway components in the form of flexible and detachable tubing 56 may be used in embodiments of the oxygen monitor 2 to provide closed gas pathway segments between the gas inlet port 36 and the air pump 34, between the air pump and the oxygen sensor module 50, and between the oxygen sensor module and the breather vent 40 (not shown in FIG. 5).

As described in more detail below, a removable dust filter 58 (shown near the top of FIG. 5) may be provided in an inlet gas pathway at a convenient location that is upstream of the oxygen sensor module 50, such as between the gas inlet port 36 and the air pump 34. As also discussed below, a magnet 60 (shown near the top right side of FIG. 5) may be disposed on an inside surface the oxygen monitor 2, such proximate to the back 8 of the housing. The magnet 60, which may be implemented as a magnetically strong neodymium N52 block (or disk) magnet, may be used for temporarily securing the oxygen monitor 2 to a surface made of ferromagnetic material, such as carbon steel.

As further shown in FIG. 5, the housing 4 may be formed as a two-component structure that includes a front housing component 4A and a rear housing component 4B. The housing components 4A and 4B may be removably attached to each other along a part line 4A-4B that is additionally shown in FIGS. 3 and 4. The housing components 4A and 4B can made from a rigid polymer (such as ABS) or other suitable material, and may be attached together in any suitable manner, including by way of removable fasteners, such as screws or the like. Two such fasteners 5 are depicted on the back 8 of the housing 4 in FIG. 2, and four more fasteners 5 are depicted on the front 6 of the housing in FIG. 1.

In FIG. 5, the housing 4 is illustrated according to an embodiment wherein the front housing component 4A (also shown in FIG. 1) and the rear housing component 4B (also shown in FIG. 2) are constructed with one or more sub-components or sub-features.

For example, the front housing component 4A may include a main front shell element 4A-1 that is apertured to provide openings for the various user interface elements described above. As a result of the main front shell element 4A-1 being apertured, this element appears intermittently at several locations on the left side of FIG. 5. As can be seen in FIG. 1, had other cross-sectional planes been illustrated (e.g., proximate to the left side 14 or right side 16 of the housing 4), the main front shell element 4A-1 would have appeared in FIG. 5 to be continuous between the top 10 and bottom 12 of the housing 4. As shown at the top of FIG. 5, the main front shell element 4A-1 may include a top end 4A-1-T that wraps around rearwardly to define a front portion of the top 10 of the housing 4. As shown at the bottom of FIG. 5, the main front shell element 4A-1 may include a bottom end 4A-1-B that wraps around rearwardly to define a front portion of the bottom 12 of the housing 4. The top end 4A-1-T and the bottom end 4A-1-B of the main front shell element 4A-1 are additionally shown in FIGS. 1, 3 and 4. FIGS. 1, 3 and 4 further depict a corresponding left side 4A-1-L and a right side 4A-1-R of the main front shell element 4A-1 that respectively wrap around rearwardly to respectively define a front portion of the left side 14 of the housing 4 and a front portion of the right side 16 of the housing. It will be appreciated that the foregoing configuration results in the main front shell element 4A-1 having a tray-like configuration with relatively shallow walls.

As shown near the top left side of FIG. 5, a top end of the main front shell element 4A-1 may be covered by, or integrally formed with, a secondary front shell element 4A-2 that provides a raised panel on the front 6 of the housing 4. As can be seen in FIG. 1, the secondary front shell element 4A-2 may be centrally located between the left side 14 and right side 16 of the housing 4. As shown near the top of FIG. 5, a top end 4A-2-T of the secondary front shell element 4A-2 may wrap rearwardly around the top end 4A-1-T of the main front shell element 4A-1. It will be appreciated that the foregoing configuration results in the secondary front shell element 4A-2 having an L-shaped configuration. In an embodiment, the secondary shell element 4A-2 may be formed wholly or partially of a transparent material. This provides, in combination with an underlying opening in the main front shell element 4A-1, the display window 20 that allows viewing of the underlying display 24, as previously described.

With continuing reference to FIG. 5, the rear housing component 4B may include a rigid main rear shell element 4B-1 that mates with the main front shell element 4A-1 around the periphery of each shell element at the part line 4A-4B. The main rear shell element 4B-1 may be covered by a thinner secondary rear shell element 4B-2 that follows the contour of the main rear shell element. In an embodiment, the secondary rear shell element 4B-2 may be formed as a rubberized finish coating in order to provide a soft surface on the back side 8 of the oxygen monitor 2 that can be more easily held by a user. In an alternate embodiment (not shown), the secondary rear shell element 4B-2 could be dispensed with if so desired. Insofar as the secondary rear shell element 4B-2 completely covers the main rear shell element 4B-1, only the secondary rear shell element is visible from outside the housing 4, and this is shown in FIGS. 2, 3 and 4.

At the bottom of FIG. 5, the main rear shell element 4B-1 and the secondary rear shell element 4B-2 may include respective bottom ends 4B-1-B and 4B-2-B that wrap around frontwardly to define a rear portion of the bottom 12 of the housing 4. As shown in FIGS. 3 and 4, this rear portion of the bottom 12 defined by the bottom ends 4B-1-B and 4B-2-B mates with the front portion of the bottom 12 defined by the bottom end 4A-1-B of the main front shell element 4A-1.

In the cross-section represented by FIG. 5, which is taken along the centerline of the gas inlet port 36, the main rear shell element 4B-1 and the secondary rear shell element 4B-2 terminate below the top 10 of the housing 4 in order to define a user-access compartment 62 wherein the dust filter 58 resides. The user-access compartment 62 is described in more detail below in connection with FIGS. 10A and 10B. In FIG. 5, a central top section 4B-1-CT of the main rear shell element 4B-1 transitions 90 degrees frontwardly to form a transverse bottom wall 64 of the user-access compartment 62. At a front end of the transverse bottom wall 64 (proximate to the part line 4A-4B), the main rear shell element 4B-1 transitions 90 degrees upwardly toward the top 10 of the housing 4 to form a transverse front wall 65 of the user-access compartment 62. As can be seen near the top right side of FIG. 5, the secondary rear shell element 4B-2 terminates where the main rear shell element 4B-1 begins its 90 degree transition to form the central top section 4B-1-CT.

Although not shown in FIG. 5, the top ends of the main rear shell element 4B-1 and the secondary rear shell element 4B-2 that lie laterally outboard of the user-access compartment 62 are similar in construction to the bottom ends 4B-1-B and 4B-2-B of the main rear shell element and the secondary rear shell element. In particular, each wraps around forwardly to define rear portions of the top 10 of the housing 4. The main rear shell element 4B-1 and the secondary rear shell element 4B-2 also include respective left and right sides that wrap around forwardly to define rear portions of the left side 14 and right side 16 of the housing 4. Insofar as the secondary rear shell element 4B-2 completely covers the main rear shell element 4B-1, only the top end 4B-2-T, the left side 4B-2-L and the right side 4B-2-R of the secondary rear shell element are visible in FIGS. 2, 3 and 4. It will be appreciated that the foregoing configuration results in the main rear shell element 4B-1 and the secondary rear shell element 4B-2 having a tray-like configuration with walls that are relatively shallow, albeit deeper than the walls of the main front shell element 4A-1.

As further shown on the right side of FIG. 5, the rear component 4B of the housing 4 may additionally mount a pivotally-mounted flip stand 66 and a removable user-access compartment cover 68. As additionally shown in FIGS. 2, 3 and 4, the flip stand 66 may be secured to the secondary rear shell element 4B-2 at a central location on the back 8 of the housing 4. It can be made from the same rigid material as the front and rear housing components 4A and 4B. Although the flip stand 66 is optional, it provides the advantage of allowing the oxygen monitor 2 to be placed in a raised non-horizontal position during oxygen monitoring operations, so that the oxygen monitor's display 24 is more easily viewed by welding personnel. The user-access compartment cover 68, which can be made of the same material as the front and rear housing components 4A and 4B, is removably mounted to the top 10 of the housing 4. It is configured to enclose the user-access compartment 62, and also mounts the gas inlet 36 and the breather vent 40. The user-access compartment cover 68 is described in more detail below in connection with FIGS. 7-9, and 10A-10B.

Figure 8:
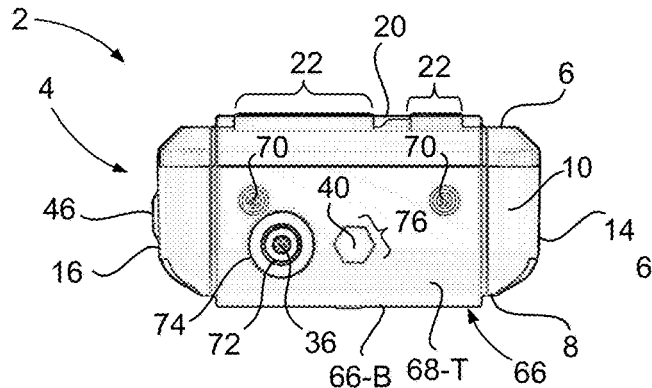
FIG. 8 is a top end view of the oxygen monitor of FIG. 1.
Figure 9:
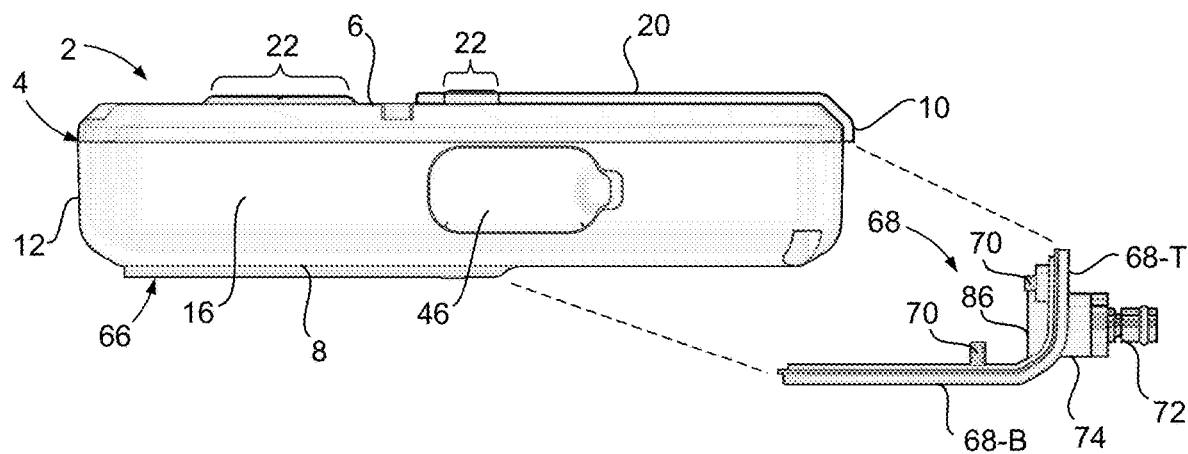
FIG. 9 is a right side elevation view of the oxygen monitor of FIG. 1, with a removable cover of the oxygen monitor housing being detached therefrom.

Turning now to FIGS. 7-9, an example construction of the user-access compartment cover 68 will now be described. As best shown in FIG. 9, the user-access compartment cover 68 may be formed as an angled L-shaped member having a top side 68-T (forming part of the top 10 of the housing 4) and a back side 68-B (forming part of the back 8 of the housing). The user-access compartment cover 68 may be attached to the remainder of the housing 4 in any suitable manner, including by way of removable fasteners 70, such as screws or the like. As may be seen in FIGS. 7 and 8, two fasteners 70 may be provided on the top side 68-T of the user-access compartment cover 68. As may be seen in FIGS. 2 and 9, two additional fasteners 70 may be provided on the back side 68-B of the user-access compartment cover 68.

It will be seen in FIG. 7 that the gas inlet port 36 may be formed as part of a male quick-connect fitting 72. The quick-connect fitting 72, which defines the entrance of the gas inlet port 36, may be mounted to a short gas inlet stem 74 formed on the top side 68-T of the user-access compartment cover 68. The breather vent 40 may be formed as a fitting that also protrudes from the top side 68-T of the user-access compartment cover 68. In the illustrated embodiment, the breather vent 40 has a hexagonal configuration in which one breather port 76 may be formed on one or more sides, thereby providing up to six individual breather ports. Other breather vent configurations are also possible.

Turning now to FIGS. 10A-10B, the user-access compartment cover 68 is shown following its detachment from the housing 4. It will be seen that the magnet 60 can be conveniently mounted to the inside surface of the user-access compartment cover's back side 68-B. The user-access compartment cover 68 may be easily removed by a user of the oxygen monitor 2, and doing so provides access to the user-access compartment 62. Removably disposed within the user-access compartment 68 is the dust filter 58 previously mentioned in connection with FIG. 5. In the illustrated embodiment, the dust filter 58 may be embodied as a sintered metal filter element, made from bronze or the like, and configured as a disk. Its function is to remove dust and other particulates from the incoming gas, thereby protecting the components of the air pump 34 (such as its diaphragm) from damage. A short gas inlet filter receptacle 78 of tubular shape may be formed on the transverse bottom wall 64 of the user-access compartment 62 in order to hold the dust filter 58. In FIG. 10A, the dust filter 58 has been removed from the filter receptacle 78 for cleaning or replacement. In FIG. 10B, the dust filter 58 has been installed in the filter receptacle 78 in an operational position.

Figure 11:
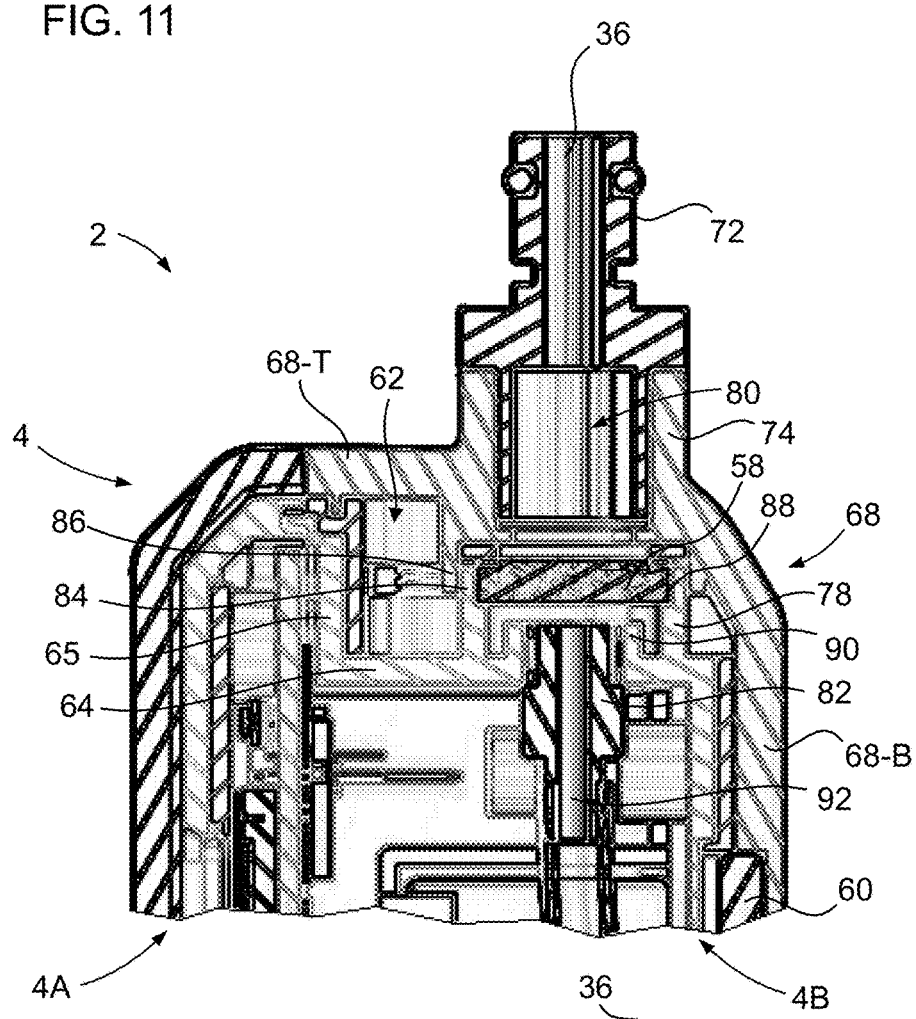
FIG. 11 is an enlarged partial cross-sectional view showing a portion of the cross-sectional view of FIG. 5.
Figure 12:
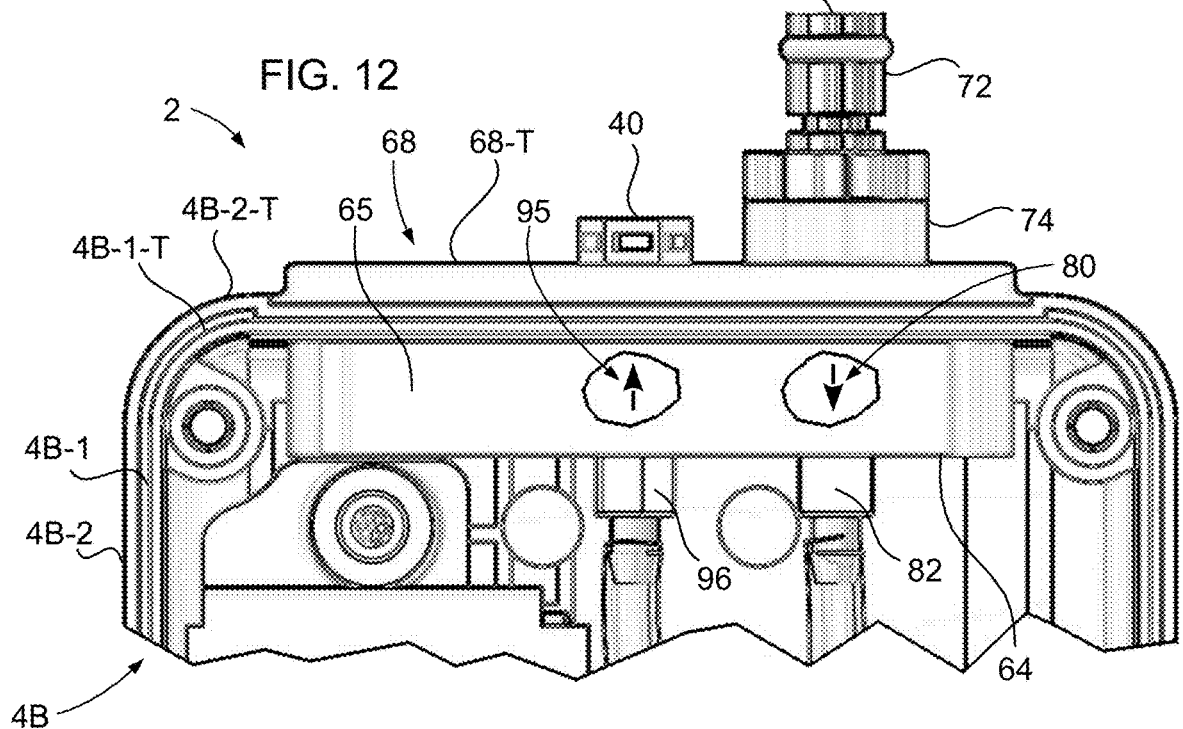
FIG. 12 is an enlarged partial plan view of the oxygen monitor of FIG. 1, with a top cover portion of thereof removed to illustrate part of a bottom cover portion and components therein, the components including a gas inlet pathway and a gas outlet pathway.

As can be seen in FIG. 11, the filter receptacle 78 forms part of a gas inlet pathway 80 that extends from the gas inlet 36, through the quick-connect fitting 72, the gas inlet stem 74, and the filter element 58 disposed in the filter receptacle 78, to an internal gas inlet fitting 82 that is mounted to (and transfixes) the transverse bottom wall 64 of the user-access compartment 62. The gas inlet fitting 82 is additionally shown in FIG. 12. FIG. 12 also illustrates the flow direction of the gas inlet pathway 80, which is shown diagrammatically beneath the transverse front wall 65 of the user-access compartment 62. The gas inlet pathway 80 provides a closed gas pathway (in part) by virtue of a free end 84 of the filter receptacle 78 being received within a tubular socket 86 formed on an interior surface of the user-access compartment cover 68. This interconnection is made when the user-access compartment cover 68 is attached to the housing 4. The tubular socket 86 is also visible in FIGS. 9, 10A and 10B. The dust filter 58 may be supported within the filter receptacle 78 by an inside annular shoulder 88 of the filter receptacle. The internal gas inlet fitting 82 may be mounted in any suitable manner to the transverse bottom wall 64 of the user-access compartment 62, such as by threaded engagement therewith. A short tubular boss 90 may be formed on the transverse bottom wall 64 to help support the internal gas inlet fitting 82. Although not shown, the boss 90 may be formed with internal threads that engage corresponding external threads on the internal gas inlet fitting 82. The internal gas inlet fitting 82 is formed with an internal through-bore 92 whose terminal end forms a gas inlet orifice representing an interior end of the gas inlet pathway 80.

Returning now to FIGS. 10A-10B, the breather vent 40 connects to a gas outlet port 94 of tubular shape when the user-access compartment cover 62 is installed. The gas outlet port 94 forms part of a gas outlet pathway 95 that is shown diagrammatically in FIG. 12 beneath the transverse front wall 65 of the user-access compartment 62. FIG. 12 illustrates the flow direction of the gas outlet pathway 95. Although not completely shown in FIG. 12, the gas outlet pathway 95 extends from the breather vent 40 to an internal gas outlet fitting 96 that is mounted in the same manner as the internal gas inlet fitting 82 shown in FIG. 11 (i.e., to the transverse bottom wall 64 of the user-access compartment 62). Also not shown in FIG. 12 is the fact that the gas outlet port 94 is received within a tubular socket on an interior surface of the user-access compartment cover 68 when the cover is attached to the housing 4. This tubular sleeve is identical in construction to the tubular socket 86 shown in FIG. 11 that engages the filter receptacle 78. The gas outlet pathway 95 thus provides a closed gas pathway between the breather vent 40 and the internal gas outlet fitting 96. The latter is formed with an internal through-bore (not shown) whose terminal end forms a gas outlet orifice representing an interior end of the gas outlet pathway 95.

As will now be described, the closed gas inlet pathway 80 and the closed gas outlet pathway 95 connect to configurable internal gas pathway components. In an embodiment, the configurable internal gas pathway components may take the form of flexible removable gas line conduits that may be implemented using the previously-mentioned flexible detachable gas line tubing 56. The tubing 56 is disposed internally within the housing 4 and extends the respective gas inlet and gas outlet pathways 80 and 95. These internal gas pathway components deliver and receive gas flow to and from the oxygen sensor module 50 mentioned above in connection with FIG. 5. Inlet and outlet gas flow is directed in a sequestered manner that prevents the mixing of inflow and outflow gases that could otherwise occur if a common sensor chamber was used for the inlet and outlet gasses, as is common practice in some oxygen monitors. This reduces the volume of gas that needs to be drawn into the oxygen monitor by the air pump 34 to obtain gas sample oxygen measurements, resulting in faster response. In an embodiment, the tubing used to form the internal gas pathway components may only be required to deliver a gas flow as low as 0.6 to 0.8 1 pm, where "1 pm" refers to liters per minute. Eschewing a common sensor chamber (which must be constructed in an airtight manner) in favor of using flexible removable gas flow pathways also makes it easier to remove and replace the oxygen sensor(s) 52, thereby facilitating modularity.

As previously noted, the oxygen monitor 2 is designed to implement a modular sensor system. Embodiments of the oxygen monitor 2 allow customization of the oxygen sensor configuration whereby different oxygen sensor modules 50, each having its own set of one or more oxygen sensors 52, may be easily removed from the oxygen monitor and replaced. Each such embodiment configured with its own customized oxygen sensor configuration may likewise include its own internal gas pathway configuration.

Turning now to FIGS. 13-16, an example embodiment of the oxygen monitor 2 is shown in which an oxygen sensor module 50A includes an optical oxygen sensor 52A having a sensitivity that allows it to detect oxygen levels ranging from atmospheric (normally approximately 20.9 vol. % or 209,000 ppm at sea level) down to approximately 100 ppm (0.01 vol. %), where "ppm" refers to parts-per-million by volume. FIG. 13 depicts the rear housing component 4B after the front housing component 4A has been separated therefrom and the circuit board 26 has been lifted off to reveal the underlying components of the housing 4.

As shown in FIG. 13, the oxygen sensor module 50A is removably mounted in the rear housing component 4B by way of two slotted module holders 98. The module holders 98 may be secured to an underlying frame 100 mounted on the rear housing component 4B. The oxygen sensor 52A includes a gas inlet port 52A-I and a gas outlet port 52A-O. As shown in FIGS. 14-15, the oxygen sensor 52A may be mechanically connected to the oxygen sensor circuit board 54 by pair of stand-offs 102. Although not shown, electrical wiring pins may extend through the standoffs to make electrical connections to the oxygen sensor circuit board 54. A plug-in connector 55 may be provided on the circuit board 54 for making electrical connections (e.g., via a cable) between the oxygen sensor module 50A and the oxygen monitor's main circuit board 26. The oxygen sensor circuit board 54 may be formed with two pairs of oxygen sensor pin holes for mounting two different oxygen sensors. One set of four mounting holes 54A that is not occupied by an oxygen sensor in the illustrated embodiment is shown in FIG. 16. A complimentary set of four mounting is used by the oxygen sensor 52A, and is therefore not visible in FIG. 16. As can be further seen in FIG. 16, the oxygen sensor circuit board 54 has two vertical edges 54B, each having a laterally protruding ear 54C. The vertical edges 54B slidably engage the slots of the module holders 98, and the ears 54C engage features (not shown) on the module holders that lock the oxygen sensor circuit board 54 in place. This removable mounting arrangement of the oxygen sensor module 50A facilitates oxygen sensor module interchange (preferably without the use of any tools). The oxygen monitoring characteristics of the oxygen monitor 2 (e.g., sensitivity) may thus be easily upgraded, downgraded, or otherwise modified. When it is desired to replace the oxygen sensor module 50A, the electrical connector 55 can be disconnected from its attached cable, the flexible detachable tubing 56 connected to the oxygen sensor 52A can be detached, and the oxygen sensor circuit board 54 can be slidably manipulated out of the slots of the module holders 98. A replacement oxygen sensor module 50 having the same type of circuit board 54 (and thus the same form factor) may then be inserted therein. Although not shown, it will be appreciated that alternative removable mounting configurations could also be used for interchangeably mounting different oxygen sensor modules 50 in the oxygen monitor 2.

FIG. 13 depicts the flexible detachable tubing 56 that may be used to provide the internal gas pathway components of the oxygen monitor 2 when the oxygen sensor module 50A is installed. A first internal gas pathway component includes a first flexible flexible detachable tube 104 that provides fluid communication between the orifice formed by the internal gas inlet fitting 82 (that is in fluid communication with the gas inlet port 36 via the gas inlet pathway 80) and a second orifice formed by an inlet port 106 of the air pump 34. The first tube 104 is detachable by virtue of a first end thereof being slidably connected to the internal gas inlet fitting 82 and a second end thereof being slidably connected to the air pump's inlet port 106. A second internal gas pathway component further includes a second flexible detachable tube 108 that provides fluid communication between an orifice formed by an outlet port 110 of the air pump 34 and an orifice formed by the gas inlet port 52A-I of the oxygen sensor 52A. The second tube 108 is detachable by virtue of a first end thereof being slidably connected to the air pump's outlet port 110 and a second end thereof being slidably connected to the oxygen sensor's gas inlet port 52A-I. A third internal gas pathway component includes a third flexible detachable tube 112 that provides fluid communication between an orifice formed by the gas outlet port 52A-0 of the oxygen sensor 52A and an orifice formed by the internal gas outlet fitting 96 (that is in fluid communication with the breather vent 40 via the gas outlet pathway 95). The third tube 112 is detachable by virtue of a first end thereof being slidably connected to the oxygen sensor's gas outlet port 52A-0 and a second end thereof being slidably connected to the internal gas outlet fitting 96. FIG. 17 illustrates the closed gas flow through the various gas-handling components of FIG. 13, from the inlet gas port 36, through the air filter 58, through the air pump 34, through the oxygen sensor 52A, to the breather vent 40.

Turning now to FIGS. 18-22, an example embodiment of the oxygen monitor 2 is shown in which an oxygen sensor module 50B includes a solid-electrolyte (e.g., yttria-doped zirconia) oxygen sensor 52B having a sensitivity that allows it to detect oxygen levels ranging from approximately 0.1 vol. % or 1000 ppm) down to approximately 5 ppm (0.0005 vol. %), where "ppm" refers to parts-per-million by volume. As shown in FIG. 18, the oxygen sensor 52B may be connected to the same flexible detachable tubing 56 described above in connection with FIG. 13 to provide the same internal gas pathway components. As shown in FIGS. 19-21, the same oxygen sensor circuit board 54 may be used to mount the oxygen sensor 52B. As shown in FIGS. 19-20, instead of two standoffs 102 being used to mount the oxygen sensor 52B to the oxygen sensor circuit board 54, four electrical pins 103 may be provided that insert directly into one set of the circuit board mounting holes 54A. As shown in FIG. 21, the set of circuit board mounting holes 54A occupied by the oxygen sensor 52B is the set that was visible in FIG. 16, whereas the set of mounting holes 54A that was occupied by the oxygen sensor 52A in FIG. 16 is now visible in FIG. 21. FIG. 22 illustrates the closed gas flow through the various gas-handling components of FIG. 18, from the inlet gas port 36, through the air filter 58, through the air pump 34, through the oxygen sensor 52B, to the breather vent 40.

Turning now to FIGS. 23-27, an example embodiment of the oxygen monitor 2 is shown in which an oxygen sensor module 50C includes both the optical oxygen sensor 52A of FIGS. 13-16 and the solid-electrolyte oxygen sensor 52B of FIGS. 18-21. The combination of the two oxygen sensors 52A and 52B enables oxygen sensing over a wide range of oxygen levels, with the optical oxygen sensor 52A detecting oxygen levels ranging from atmospheric (normally approximately 20.9 vol. % or 209,000 ppm at sea level) down to approximately 100 ppm (0.01 vol. %), and with the solid-electrolyte oxygen sensor 52B detecting oxygen levels ranging from approximately 0.1 vol. % or 1000 ppm) down to approximately 5 ppm (0.0005 vol. %), where "ppm" refers to parts-per-million by volume. In this dual oxygen sensor embodiment, the oxygen monitor 2 may selectively utilize the optical oxygen sensor 52A for the high end of the oxygen content range, then switch to the solid-electrolyte oxygen sensor 52B for the low end of the oxygen content range.

As shown in FIG. 23, the oxygen sensors 52A and 52B may be connected to some of the same flexible detachable tubing 56 described above in connection with FIGS. 13 and 18 to provide the same internal gas pathway components, with one modification. In particular, an additional internal gas pathway component includes a flexible detachable tube 114 that provides fluid communication between the orifice formed by the gas outlet port 52B-0 of the solid electrolyte oxygen sensor 52B to the orifice formed by the gas inlet port 52A-I of the optical oxygen sensor 52B. The tube 114 is detachable by virtue of a first end thereof being slidably connected to the gas outlet port 52B-0 of the oxygen sensor 52B and a second end thereof being slidably connected to the gas inlet port 52A-I of the oxygen sensor 52A.

FIGS. 24-26 illustrate how the oxygen sensors 52A and 52B may be mounted on the oxygen sensor circuit board 54. FIG. 27 illustrates the closed gas flow through the various gas-handling components of FIG. 23, from the inlet gas port 36, through the air filter 58, through the air pump 34, through the solid electrolyte oxygen sensor 52B, through the optical oxygen sensor 52A, to the breather vent 40. Note that the order in which the oxygen sensors 52A and 52B are placed in the gas flow pathway may be reversed is so desired.

It will be appreciated, from the three embodiments described above in connection with FIGS. 13-17, 18-22, and 23-27, that the oxygen monitor 2 may be easily modified to provide different oxygen sensor modules 50 (e.g., 50A, 50B or 50C) with different oxygen sensing capabilities. Modifying the oxygen monitor 2 is a simple matter of slidably removing an existing oxygen monitor module 50 from the module holders 98 and slidably inserting a new oxygen monitor module. It should be understood that other types of oxygen sensors may also be used for providing oxygen sensors with different capabilities. The illustrated use of the optical and solid-electrolyte sensors 52A and 52B having specified oxygen sensing ranges (as previously described) represents only one possible implementation of the oxygen monitor 2.

Figure 28:
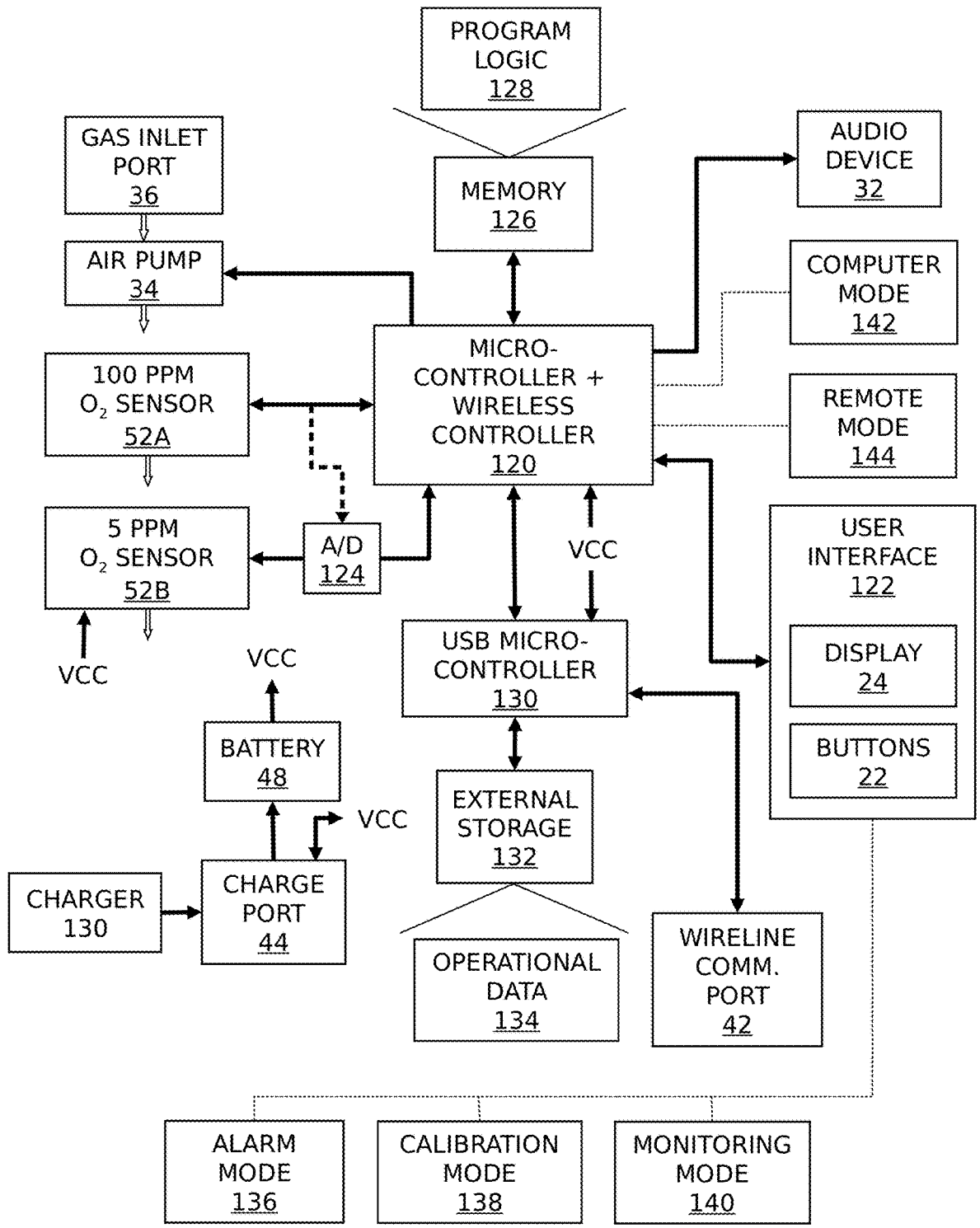
FIG. 28 is a functional block diagram showing example functional components of the portable hand-held oxygen monitor of FIG. 1.

Turning now to FIG. 28, a functional block diagram of the oxygen monitor 2 is shown. In this embodiment, the operations of the oxygen monitor 2 are managed by a main controller 120 that may include both micro-controller and wireless controller functionality. The main controller 120 is in electrical communication with several different components, namely, (1) the user interface (shown by reference number 122 in FIG. 28) that includes the display 24 and the user interface buttons 22, (2) the air pump 34, (3) the optical oxygen sensor 52A (if present), (4) the solid-electrolyte oxygen sensor 52B (if present), (5) an associated A/D (analog-to-digital) converter 124 (e.g, on the oxygen sensor circuit board 54), (6) the audio device 32, the (7) the battery 48, and (8) and the charge port 44, which can be connected to an external charger 130. Either the battery 48 or the charge port 44 may be used a source of VCC positive supply voltage for the oxygen monitor 2, depending on whether or not the charge port 44 is receiving power from the charger 130. In an embodiment, the 100 ppm oxygen sensor 52A may be a digital sensor with an integrated A/D converter, such that the illustrated A/D converter 124 may only be needed for the 5 ppm oxygen sensor 52B. Alternatively, the 100 ppm oxygen sensor 52A may be an analog sensor, in which case it may utilize the A/D converter 124.

In the illustrated embodiment, the main controller 120 is additionally in electrical communication with a memory 126 that may be implemented using any of a variety of micro-controller memory technologies. The memory 126, which could be situated on-chip with the main controller, may include a combination of non-volatile (e.g., flash) code memory and volatile (e.g., RAM) data memory. The code memory component of the memory 126 represents a non-transitory computer-readable data storage medium that may be used to store program logic 128 in digital form (e.g., firmware). The micro-controller component of the main controller 120 executes the program logic 128 in order to perform program operations that manage various functions of the oxygen monitor 2. The volatile data memory component of the memory 126 may be used to store different types of program data, such as temporary variables, global variables, program stack and heap sections.

In the illustrated embodiment, the main controller 120 is also in electrical communication with a USB micro-controller 130 that connects to the wireline communication port 42 (described above in connection with FIG. 4) and to an external data storage 132, such as an SD (Secure Digital) card. The external storage 132 may be used to store operational data 134 generated during operation of the oxygen monitor 2, such as gas sample logging data and runtime state information. The operational data 134 may also include static system information, such as operational settings and parameters.

As noted above, the main controller 120 may include wireless controller functionality. The wireless controller provides a wireless communication interface that supports digital wireless communication using a suitable communication protocol. Example wireless interface technology that may be supported by the wireless controller include Bluetooth®, BLE (Bluetooth®low energy), WiFi, Cellular, etc.

As previously noted, the program logic 128 stored in the memory 126 is used to program the micro-controller component of the main controller 120 to perform various functions and operations. These functions and operations include various operational modes, namely, an alarm mode 136, a calibration mode 138, an oxygen monitoring mode 140, a computer mode 142 and a remote mode 144. With the exception of the computer mode 142 and the remote mode 144, each of these operational modes is implemented by the main controller 120 in response to activation of one or more of the user interface buttons 22. The computer mode 142 is activated by connecting a remote computer (such as a PC) to the wireline communication port 42. The remote mode 144 is activated by a remote device initiating wireless communication with the oxygen monitor 2. Example embodiments of the computer mode 142 and the remote mode 144 are described in more detail below.

The monitoring mode 140 is invoked by pressing the pump button 22C, as previously noted. Example embodiments of this operational mode are described in more detail hereinafter.

The alarm mode 136 and the calibration mode 138, are invoked by pressing the menu button 22D (FIG. 1) and selecting corresponding menu options. Thus, it is appropriate at this point to briefly discuss the various menu options that the button 22D may be configured to provide. FIGS. 29A and 29B illustrate an embodiment wherein the menu button 22D is used to display an options menu 144 on the display 24. Desired menu options are reached using the menu-up scroll button 22E and the menu-down scroll button 22F to scroll through the selections, and then pressing the menu button 22D to select the option of interest. Three of the options, respectively labeled "Languages," "Date & Time," and "Device Info.," are used to select and/or view general operational characteristics and preferences for the oxygen monitor 2. For example, the Languages menu option (shown in FIG. 29A) allows a user to select the language used for displayed text. The Date & Time menu option (shown in FIG. 29A) allows a user to set the current date and time. The Device Info. menu option (shown in FIG. 29B) allows a user to view oxygen monitor system information, such as unit serial number, hardware version, firmware version, manufacturing data, oxygen sensor serial number, factory calibration values, current calibration values, calibration dates, etc. FIG. 29B-1 depicts an example system information screen 145 that may be displayed when the Device Info. menu option is selected. In this example, the system information includes oxygen monitor model number, the current HI CAL and LO CAL (see below) calibration values along with the dates and times when the HI CAL and LO CAL calibration operations were most recently performed, the oxygen monitor unit serial number, and the oxygen sensor serial number.

The remaining menu options displayed by the options menu 144 of FIGS. 29A and 29B are labeled "Alarm," "Logging," and "Calibration." The Alarm menu option is used to select the alarm mode 136 of the oxygen monitor 2. The alarm mode 136 allows a user to specify an oxygen level that will trigger an alarm output during the oxygen monitoring mode 140. The alarm may take the form of an audible alert that is output by the audio sound generator device 32, and (optionally) also a visual alarm that may be output by the display 24. When the Alarm option is invoked in the options menu 144, the main controller 120 may present a range of suggested oxygen level alarm values for selection by a user via the user interface 22. In an embodiment, both a High alarm value and a Low alarm value may be set. The High alarm value represents a maximum acceptable oxygen level (e.g., 8000 ppm) that the user considers to be safe for welding, and the Low alarm value represents a critical target oxygen level (e.g., 1000 ppm or less) that the user considers to be ideal. A distinctive alarm sound may generated when the critical Low alarm threshold is crossed, and (optionally) when the High alarm threshold is crossed. Corresponding visual alarms may also be generated depending on whether the oxygen content of the incoming gas samples is above the High alarm threshold, between the High and Low alarm thresholds, or below the Low alarm threshold. For example, the display 24 could initially depict a first background color (e.g., red) that changes to a second background color (e.g., amber) as the High alarm threshold is reached, and then changes to a third background color (e.g., green) as the Low alarm threshold is reached.

FIGS. 30A, 30B and 30C illustrate how the High alarm and Low oxygen level alarm values may be used to generate alarms during the oxygen monitoring mode 140 of the oxygen monitor 2. In the oxygen monitoring mode 140, the display 24 depicts oxygen level monitoring information 146 in real time. FIG. 30A depicts the start of oxygen monitoring when a gas being sampled by the oxygen monitor 2 has a standard atmospheric oxygen concentration of 20.90% or 209,000 ppm (at sea level). In this stage of oxygen monitoring, the display 24 depicts a first background color (e.g., red). FIG. 30B depicts a later stage of oxygen monitoring when gas being sampled by the oxygen monitor 2 has a reached an oxygen concentration of 0.80% or 8,000 ppm. Assuming this corresponds to the High alarm value set by the user, the display 24 will depict a second background color (e.g., amber). FIG. 30C depicts a further stage of oxygen monitoring when gas being sampled by the oxygen monitor 2 has a reached an oxygen concentration of 0.10% or 1,000 ppm. Assuming this corresponds to the Low alarm value set by the user, the display 24 will depict a third background color (e.g., green).

Returning now to FIGS. 29A and 29B, the Logging menu option allows a user to view logging data collected by the oxygen monitor during the oxygen monitoring mode 140. In an embodiment, only a subset of the logging data may be reviewable, such as the last 50 data points. Logging is described in more detail below.

The Calibration menu option (shown in FIG. 29B) is used to select the calibration mode 138 of the oxygen monitor 2. When the calibration mode 138 is invoked, the calibration sub-menu 148 depicted in FIG. 31 may be generated on the display 24. The sub-menu 148 allows two-point calibration operations to be performed on the 100 ppm oxygen sensor 52A. As noted above, this is an optical oxygen sensor. The 5 ppm oxygen sensor 52B, which is a solid electrolyte oxygen sensor, will typically be factory calibrated, such that no user calibration is required. A HI CAL menu option is used to calibrate a 20.9% atmospheric oxygen level point of the oxygen sensor 52A. Ambient air may be used for this procedure. A LO CAL menu option is used to calibrate a 0% oxygen level point of the oxygen sensor 52A. A source of 99.999% argon gas may be used for this procedure. When either of these menu options is selected, the main controller 120 activates the air pump 34 to draw a gas sample into the gas inlet port 36, and deliver the sample via the previously-described gas line tubing 56 to the oxygen sensor module 50 that carries the oxygen sensor 52A. As described above in connection with FIGS. 13 and 23, this may be either the module 50A or 50C, depending on which is installed in the oxygen monitor 2. The oxygen sensor 52A detects the amount of oxygen in the gas sample, and generates an analog oxygen sensor output having a corresponding voltage level. After appropriate analog-to-digital conversion of the voltage level, the oxygen sensor output is input to the main controller 120 and stored in the the external storage 132 as a calibration oxygen level value that represents part of the oxygen monitor's operational data 134. Once calibration is complete, the calibration operation can be verified by selecting the Device Info. Menu option described above in connection with FIGS. 29B and 29B-1. If calibration was successful, the oxygen monitor 2 will be ready to accurately determine the oxygen content of gas samples obtained during the oxygen monitoring mode 140.

Figure 32:
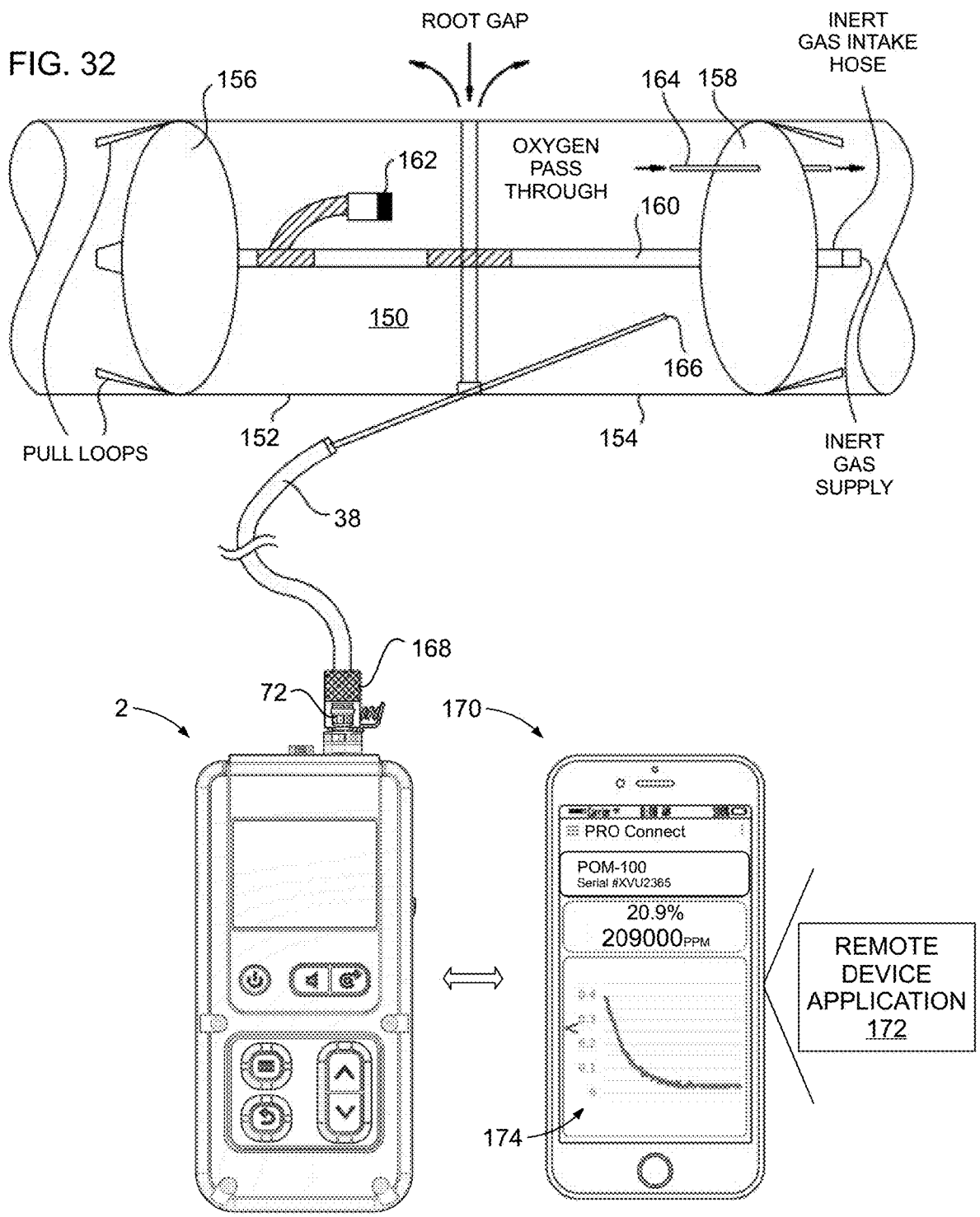
FIG. 32 is a diagrammatic illustration showing the oxygen monitor of FIG. 1 being used to monitor oxygen in a weld zone during a pipe-welding purge operation, and while the oxygen monitor is in wireless communication with a remote device that implements a remote device display to provide a user interface that displays data received from the oxygen monitor.

Turning now to FIG. 32, the oxygen monitor 2 is shown during the monitoring mode 140 as it monitors oxygen in a pipeline weld zone 150 during a weld zone purging operation. In FIG. 32, a pair of pipes 152/154 are to be butt-welded together at a welding root gap. A purge dam apparatus installed within the pipes has first and second pipe blocking members 156 and 158 that, for purposes of example only, may be implemented as inflatable purge bladders. The purge bladders 156 and 158 are joined together by an intermediate bridge conduit 160. FIG. 32 shows the purge dam apparatus after the purge bladders 156 and 158 have been inflated with an inert gas from an inert gas supply (not shown). The inert gas is fed from the inert gas supply through an inert gas intake hose connected to a port on the right-hand purge bladder 158. The inert gas inflates both purge bladders 156/158, and also flows into the weld zone 150 via a purge gas outlet port 162 connected to the bridge conduit 160. The enclosed space between the purge bladders represents the weld zone 150, which is purged of air by the purge gas following the introduction thereof through the purge gas outlet port 162. Oxygen displaced by the incoming purge gas exits the weld zone 150 via the root gap, and may also exit through a vent port 164 extending through the right-hand purge bladder 158.

As can be seen, the oxygen monitor 2 is operable to obtain oxygen readings from the weld zone 150 using a detachable probe 38. A rigid probe tip 166 at the inlet end of the probe 38 is inserted into the root gap so that it can draw gas samples from the weld zone 150. The probe tip 166 can be made of steel or other material that can withstand the heat from the welding operation. Advantageously, the probe tip 166 is long so that it can collect gas samples from deep in the weld zone 150. Preferably, the probe tip 166 is at least approximately 100 mm long so that it can will reach the centerline of a pipe having a diameter of 200 mm. More preferably, the probe tip 166 will be longer so that it can probe the side regions of the weld zone 150, as shown in FIG. 32. In an example embodiment, the probe tip 166 is at least approximately 160 mm in length. The probe tip 166 is also as thin as possible while still being capable of drawing gas samples in order to minimize root gap width. Preferably, the outside diameter of the probe tip 166 will not exceed approximately 5 mm. In an example embodiment, the probe tip 166 has an outside diameter of not more than approximately 2 mm, with an inside diameter of approximately 1 mm. The base end of the probe 38 has an enlarged fitting 168 that mounts to one end of a flexible tube portion of the probe 38. The fitting 168 removably connects to the quick-connect fitting 72 of the oxygen monitor 2, which defines the entrance of the oxygen monitor's gas inlet port 36.

As previously noted, the oxygen monitoring mode 140 is invoked by pressing the pump button 22C (FIG. 1) to actuate the underlying pump switch 28C (FIG. 6) on the circuit board 26. When the pump button is pressed, the air pump 34 draws a gas to be sampled through the probe 38 and into the inlet gas port 36. The gas is delivered via the previously-described gas line tubing 56 to the oxygen sensor module 50, which may be one of the modules 50A, 50B or 50C depending on which is installed in the oxygen monitor 2. Each of the oxygen sensors 52A, 52B and 52C is designed to detect the amount of oxygen in the gas and output a corresponding analog voltage level that is A/D converted to a digital gas sample oxygen level value, processed by the main controller 120, and output to the display 24. Each discrete gas sample oxygen level value processed by the main controller 120 may be referred to as a "gas sample reading." If the alarm mode 136 is active, the main controller 120 may compare the gas sample reading to the High and Low alarm values, and activate an alarm when the gas sample oxygen level value reaches each specified alarm threshold. As previously described, the alarm activation may include changing the background color of the display 24 and generating a sound from the audio device 32 to alert a monitor user.

FIGS. 30A, 30B and 30C depict example gas sample readings output to the display 24. As can be seen, the gas sample readings may be displayed as an oxygen level percentage value (by volume), an oxygen level ppm value (by volume), or both. Displaying both oxygen level formats may be advantageous because some monitor users are used to working with oxygen percentage values while others are used to working with ppm values. In an embodiment, a menu option could be provided for selectively displaying oxygen percentage values and/or ppm values.

During the oxygen monitoring mode 140, the foregoing operations may be repeated periodically at predetermined intervals (e.g., every millisecond, every second, etc.) on a continuous basis, until the user discontinues oxygen monitoring by pressing the pump button 22C (FIG. 1) a second time. If the oxygen sensor module 50A or 50B is installed in the oxygen monitor 2, the oxygen detection operations performed during the monitoring mode 140 will respectively utilize either the 100 ppm oxygen sensor 52A or the 5 ppm oxygen sensor 52B. If the oxygen sensor module 50C is installed in the oxygen monitor 2, the oxygen detection operations performed during the monitoring mode 140 will initially utilize the 100 ppm oxygen sensor 52A and then transition over to the 5 ppm oxygen sensor 52B when a predetermined cross-over oxygen level reached. The cross-over oxygen level may vary, but should be greater than or equal to the minimum oxygen level that can be accurately detected by the 100 ppm oxygen sensor 52A (i.e., 100 ppm) and less than or equal to the maximum oxygen level that can be accurately detected by the 5 ppm oxygen sensor 52B (e.g., approximately 0.1 vol. % or 1000 ppm). The cross-over oxygen level may be specified in the program logic 128 of the main controller 120.

In an embodiment, the oxygen monitoring mode 140 may include data logging in which the main controller 120 stores logging event data as part of the operational data 134 in the external storage 132. Logging may be implemented automatically, with user control being limited to viewing the log data by selecting the Logging menu option shown in FIGS. 29A and 29B. If desired, the Logging menu option could also be implemented so as to allow the user to selectively enable or disable logging. As described in more detail below, the computer mode 142 of the oxygen monitor may also allow log data viewing (and deleting) via a remote computing device when the oxygen monitor 2 is connected thereto.

The logging event data may be collected and stored as a series of periodic logging events. Each logging event may capture one or more gas sample readings generated during the monitoring mode 140. Each logging event may include an associated timestamp indicating when the logging event was recorded. The one or more gas sample readings that comprise a logging event may be stored as oxygen level percentage values, as oxygen level ppm values, or both. The logging event data may also indicate whether the alarm set mode 136 was active at the time of each logging event, and if so, whether an alarm was being generated at the time of the logging event.

To conserve storage space in the external storage 132, logging events may be performed less frequently than the gas sample readings being generated and output to the display 24. The latter are designed to provide real-time viewing of continuously decreasing oxygen levels in a gas being monitored. For logging, one logging event could be performed for every "n" gas sample readings, where "n" is selected based on a desired logging event frequency taking into the account the limits on the storage space available in the external storage 132. Thus, if gas sample readings are generated and displayed once per second, a logging event could be recorded for every 15 gas sample readings, representing a 15 second time span between logging events.

Other information collected in connection with a particular welding job could also be logged. By way of example, this could include weld location information, such as a location on a pipeline or other welded structure where a weld was made and the logging data was generated. One advantage of capturing such location information would be for forensic purposes in the event of a subsequent weld failure. Although not shown, an embodiment of the oxygen monitor 2 could include a locating device, such as a GPS (global positioning system) unit, that can automatically generate the monitor location information for storage as part of the operational data 134 in the external storage 132. The automated location information could be stored as part of the logging data.

Returning now to FIG. 28, the computer mode 142 allows the oxygen monitor 2 to be connected via the digital wireline communication port 42 (see FIG. 4) to a separate computing device (not shown in FIG. 28), such as a desktop computer, a laptop computer, or a handheld mobile device such as tablet, a smartphone, etc. In an embodiment, the main controller 120 may be programmed to allow the separate computing device to mount the external storage 132, read/write the non-volatile portion of the memory 126, or both. As part of the computer mode 142, the separate computing device may be permitted to perform such operations as viewing (and possibly deleting) the logging event data in the external storage 132, viewing the Device Info. information in the external storage 132, and (as an implementation option) flashing the non-volatile code memory component of the memory 126 in order to perform firmware updates on the oxygen monitor 2 that modify its programming, etc.

With continuing reference to FIG. 28, the remote mode 144 allows the oxygen monitor 2 to be accessed and controlled by a remote computing device (not shown in FIG. 28), such as a desktop computer, a laptop computer, or a handheld mobile device such as tablet, a smartphone, etc. The main controller 120 may be programmed with an API (Application Program Interface) that allows the remote device to invoke various functions of the oxygen monitor 2 using wireless communication supported by the wireless controller portion of the main controller 120.

FIG. 32 depicts an example embodiment of a remote device 170 in the form of a smartphone that runs a remote device application 172. The remote device 170 includes a touchscreen that generates a display 174. FIG. 32 depicts the remote display 174 generating output as part of the remote mode 144 of the oxygen monitor 2, and in particular, in conjunction with the monitoring mode 140 of the oxygen monitor. This usage of the remote device 170 is described in more detail below.

In the embodiment of FIG. 32 in which the remote device 170 is implemented as a smartphone, the remote device application 172 could be a custom smartphone "app" that communicates with a corresponding custom API provided by the main controller 120 of the oxygen monitor 2. In an alternative embodiment, the main controller 120 could provide an API that utilizes generic client-server software. For example, the remote device 170 could implement a web browser client that displays on the remote device display 174 a server-generated by a webpage. The server-generated user web page could be generated by either the main controller 120 implementing a generic web server program, or by a separate web server platform (not shown) that intermediates between the oxygen monitor 2 and the remote device 170.

Figure 33:
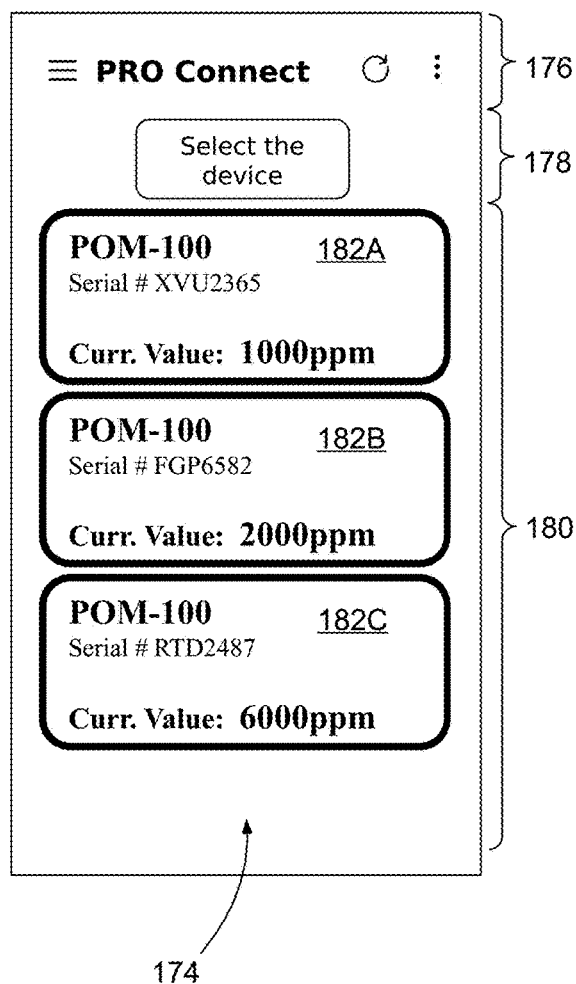
FIG. 33 is a diagrammatic illustration showing a main menu that may be displayed by a remote device that wirelessly communicates with the oxygen monitor of FIG. 1.

FIG. 33 depicts an example of how a home screen of the remote device display 174 might appear. In this home screen, the display 174 includes an upper status/navigation bar 176 that depicts the name of the remote device application 174 (e.g, "PRO Connect") and provides various menu and navigation interface components. Although not shown, these interface components may include some or all of the functions provided by the user interface buttons 22 of the oxygen monitor 2, including the ability to select the various options provided by the options menu 144 (including sub-menus) depicted in FIGS. 29A and 29B. In this way, the remote device 170 may be programmed to control some or all operational aspects of the oxygen monitor 2. The display 174 may further include an oxygen monitor selector element 178 (e.g., "Select the device") and a data area 180.

In an embodiment, the remote device application 172 may be concurrently operable with separate instances of the oxygen monitor 2, each of which may be actively engaged in oxygen monitoring. In that case, the data area 180 may depict an oxygen monitor identifier element for each oxygen monitor 2. Three such oxygen monitor identifier elements 182A, 182B and 182C are shown in FIG. 33. Each depicts the name of an oxygen monitor 2 (e.g., "POM-100") and its serial number. If the oxygen monitor 2 is actively monitoring a weld zone, and if the remote device 170 has established active communication with the oxygen monitor, the oxygen monitor identifier element 182A, 182B or 182C may also specify the value of the oxygen monitor's current gas sample reading. To interact with one of the listed oxygen monitor instances, a user may select the corresponding oxygen monitor identifier element 182A, 182B or 182C in the data area 180, then confirm the selection using the oxygen monitor selector element 178. If communication has not yet been established with the selected oxygen monitor 2, the remote device 170 may do so at this time.

Figure 34:
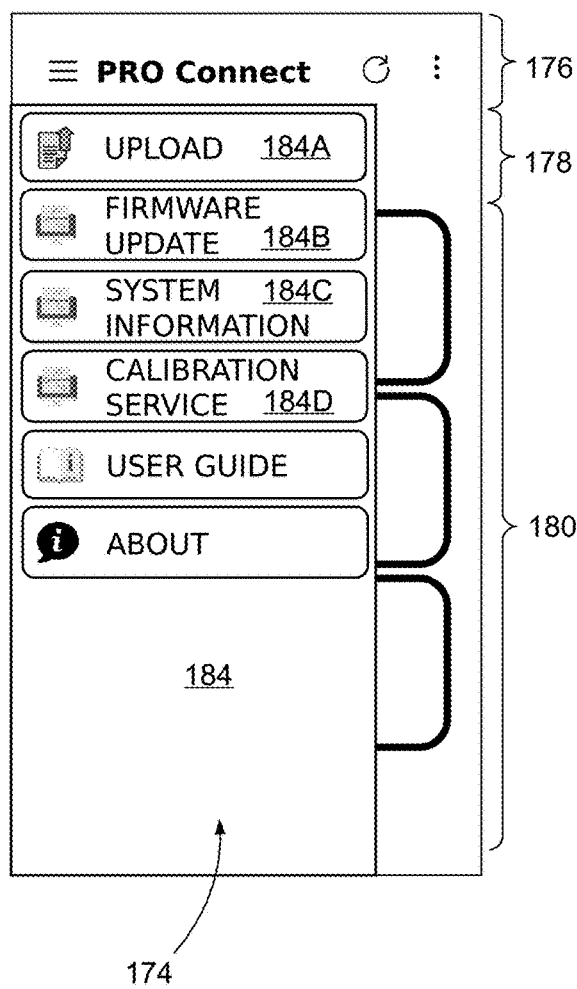
FIG. 34 is a diagrammatic illustration showing a sub-menu that may be displayed by a remote device that wirelessly communicates with the oxygen monitor of FIG. 1.

Once an oxygen monitor instance has been selected by a user in FIG. 33, the user may interact with the selected oxygen monitor 2 in several ways, depending on whether or not the oxygen monitor is in the monitoring mode 140. FIG. 34 depicts a sub-menu 184 that may be invoked by a user when the selected oxygen monitor 2 is not in its monitoring mode 140. The sub-menu 184 may be invoked via the status/navigation bar 176, and may be displayed so as to overlay the oxygen monitor selector element 178 and data area 180 of FIG. 33. The sub-menu 184 provides several user-selectable options, including an UPLOAD sub-menu option 184A, a FIRMWARE UPDATE sub-menu option 184B, a SYSTEM INFORMATION sub-menu option 184C, and a CALIBRATION SERVICE sub-menu option 184D.

Selection of the UPLOAD sub-menu option 184A allows the remote device 170 to access the file system of the oxygen monitor's external storage 132 in order to upload some or all of the operational data 134. The UPLOAD sub-menu option 184A may thus be used to acquire the oxygen monitor's logging event data for analysis at the remote device 170, or to forward the logging event data to a separate computing device, such as a desktop or laptop computer.

The FIRMWARE UPDATE sub-menu option 184B allows the remote device 170 to access the non-volatile code memory component of the oxygen monitor's memory 126 in order to perform firmware updates on the oxygen monitor that modify its programming.

The SYSTEM INFORMATION sub-menu option 184C may be used to retrieve certain operational data 134 from the oxygen monitor's external storage 132, particularly static system information and runtime state information. The oxygen monitor static system information may include the previously-described Device Info. information (see FIG. 29B). The runtime state information may include status messages, fault codes, core/stack dump data, and other troubleshooting information generated during oxygen monitor operations.

Advantageously, the SYSTEM INFORMATION sub-menu option 184C may be used to capture and store such static system and runtime state information on the remote device 170. In the event that a user of the oxygen monitor 2 reports problems in the field, the remote device 170 may be remotely queried by the oxygen monitor manufacturer using factory analytical equipment that can evaluate the static system and runtime state information obtained from the oxygen monitor in order to perform manufacturer troubleshooting. Note that the foregoing troubleshooting scenario is effective when the oxygen monitor 2 supports short range communication with the remote device 170, such as via a short range wireless connection (e.g., using machine-to-machine (M2M) Bluetooth® or BLE pairing), but does not support long range communication directly with the factory. In this scenario, the remote device 170 acts as a service agent proxy for the factory equipment to access the oxygen monitor 2 and retrieve and forward the latter's static system and runtime state information for remote analysis.

The SYSTEM INFORMATION sub-menu option 184C may also allow the remote device 170 to remotely set certain system information maintained by the oxygen monitor 2. For example, the remote device 170 could be used remotely change the date and time settings of the oxygen monitor 2. The remote device 170 could also be used to remotely reset the calibration values of the oxygen monitor 2 back to the monitor's original factory calibration values.

The CALIBRATION SERVICE sub-menu option 184D may be used to provide periodic reminders when the oxygen monitor 2 is due for factory calibration service. This is primarily applicable to the 5 ppm solid-electrolyte oxygen sensor 52B, but may also apply to the 100 ppm optical oxygen sensor 52A. By selecting the CALIBRATION SERVICE sub-menu option 184D, a user can quickly determine when the next calibration service update is due. In the event that the user forgets to check when calibration service is due, the CALIBRATION SERVICE sub-menu option 184D can provide an alert when the calibration deadline is approaching. The CALIBRATION SERVICE sub-menu option 184D may also provide the ability to request calibration from the factory via the remote device 170.

Figure 35:
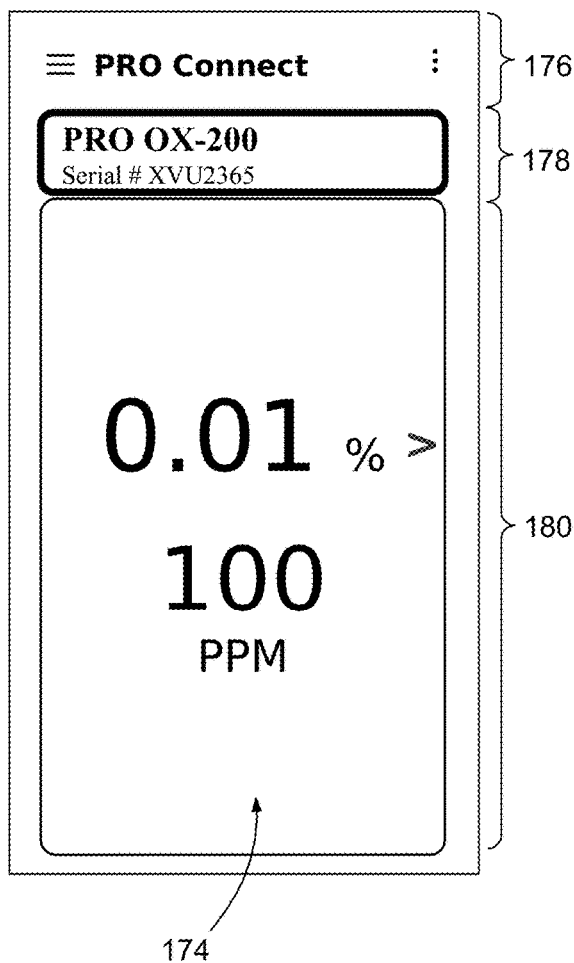
FIG. 35 is a diagrammatic view of a gas sample readings output that may be displayed by a remote device that wirelessly communicates with the oxygen monitor of FIG. 1, while the latter is engaged oxygen monitoring.
Figure 36:
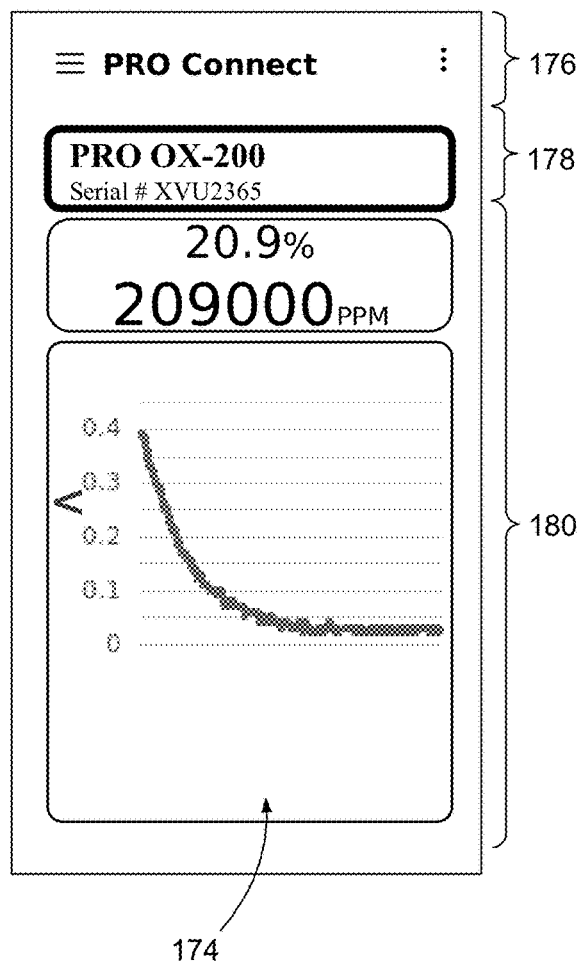
FIG. 36 is a diagrammatic plan view of an alternative gas sample readings output that may be displayed by a remote device that wirelessly communicates with the oxygen monitor of FIG. 1, while the latter is engaged oxygen monitoring.

Turning now to FIGS. 35 and 36, the display 174 of the remote device 170 is shown during an operational state in which an oxygen monitor 2 has been selected using the home screen of FIG. 33, communication has been established with the selected oxygen monitor, and the oxygen monitor has been placed in its monitoring mode 140. If the remote device 170 is communicating wirelessly with oxygen monitor 2, the remote device may be situated at any distance away from the oxygen monitor (and from the weld zone 150) that is compatible with the wireless protocol being used. For example, direct machine-to-machine (M2M) communication using Bluetooth® or BLE pairing or the like may allow communication at distances up to 100 meters. On the other hand, world-wide coverage may be provided if communication between the oxygen monitor 2 and the remote device 170 utilizes one or more intermediate devices, such as PAN, LAN, WAN or cellular network entities.

When the oxygen monitor 2 performs oxygen monitoring while in the remote mode 144, the main controller 120 of the oxygen monitor may respond to operational commands from the remote device 170, and communicate, in real-time, oxygen monitoring data consisting of some or all of the gas sample readings generated by the oxygen monitor. In some embodiments, the oxygen monitoring data transmitted to the remote device 170 may consist of all of the oxygen monitor's gas sample readings. In other embodiments, the oxygen monitoring data sent to the remote device 170 may consist of only some of the gas sample readings. For example, the transmitted oxygen monitoring data could consist of a defined subset of "n" gas sample readings out of a full set of "m" total gas sample readings generated by the oxygen monitor, where "n" is some fraction of "m," such as ½ m, ¼ m, etc. Transmitting fewer than all of the gas sample readings generated by the oxygen monitor 2 may help extend the life of oxygen monitor's battery 48. In a further embodiment, the oxygen monitor 2 may be configured to sense whether the oxygen monitor is being powered by the charger 130 (FIG. 28), and if so, transition from transmitting only some of the gas sample readings to all of the gas sample readings.

The remote device 170 may, in turn, display the gas sample readings received from oxygen monitor 2 on the remote device display 174. This facilitates remote observation of the purging operation using the remote device 170 instead of the oxygen monitor 2. The oxygen monitor 2 and the remote device 170 will thereby function as a distributed oxygen monitor system. In some cases, there may be more than one remote device 170, such as when different remote devices are used by different personnel involved in a single weld zone purging operation. In an embodiment, the remote device 170 may also perform remote device logging to log the gas sample readings in a remote device storage.

FIGS. 35 and 36 depict an embodiment in which the field 178 of the display 174 is an oxygen monitor identifier that identifies an oxygen monitor 2 selected using the main menu of FIG. 33, and whose gas sample readings are currently being displayed by the remote device 170. The data area 180 of the remote device display 174 displays the gas sample readings in alpha-numeric form. The remote device 170 may also display additional information, such as the graph in FIG. 36 that plots decreasing oxygen content versus time.

In FIGS. 35 and 36, the data area 180 of the remote device display 174 displays gas sample readings and other oxygen monitoring information using a format that is native to the remote device application 172 running on the remote device 170. In an alternate embodiment, the remote device application 172 may drive the display 174 so that the information shown in the data area 180 is formatted to mimic the output of the oxygen monitor's display 24, such as by duplicating by the display format shown in FIGS. 30A, 30B and 30C. In either case, the remote device 170 may be programmed to generate both visual and audible alarms in a manner similar to the oxygen monitor 2.

Advantageously, during initial purging of the weld zone 150 shown in FIG. 32, and prior to welding, purging personnel do not have to watch the display 24 of the oxygen monitor 2 to determine when the desired oxygen level has been reached. They may leave the weld site to perform other tasks, and check the weld zone oxygen levels via the native or emulated data area 180 of the remote device display 174 (or other remote device display). This frees welding personnel from having to remain in close proximity to the job site, allowing them to engage in other activities while waiting for the weld zone 150 to be purged. Insofar as the initial purging of a weld zone may take as long as two hours, depending on the size of the weld zone and other factors, the ability to remotely view the purging operation is highly advantageous.

For large operations in which multiple weld jobs are being performed simultaneously, the ability of the remote device application 172 to simultaneously monitor multiple oxygen monitors 2 running in the monitoring mode 140 means that supervisory personnel can easily keep track of ongoing purge operations. Moreover, the multiple oxygen monitors 2 can be managed from a single remote device 170 via the UPLOAD, FIRMWARE UPDATE, SYSTEM INFORMATION, and CALIBRATION SERVICE sub-menu options 184A, 184B, 184C and 184D, as shown in FIG. 34.

Accordingly, an oxygen monitor for monitoring oxygen in a weld zone has been disclosed, together with a distributed oxygen monitor system that includes an oxygen monitor and remote device. Reference in the present disclosure to an "embodiment" means that a particular feature, structure or characteristic described in connection with the embodiment may be included in at least one embodiment of the disclosed device. Thus, the appearances of the term "embodiment" in various places throughout the specification are not necessarily all referring to the same embodiment.

For purposes of explanation, specific configurations and details have been set forth herein in order to provide a thorough understanding of the present invention. However, it will be apparent to one of ordinary skill in the art that embodiments of the present invention may be practiced without the specific details presented herein. Furthermore, well-known features may have been omitted or simplified in order not to obscure the present invention. Various examples have been given throughout this description. These examples are merely descriptions of specific embodiments of the invention. The scope of the claimed subject matter is not limited to the examples given.

As used herein, the terms such as "upper," "lower," "top," "bottom," "vertical," "vertically," "lateral," "laterally," "inner," "outer," "outward," "inward," "front," "frontward," "forward," "rear," "rearward," "upwardly," "downwardly," "inside," "outside," "interior," "exterior," and other orientational descriptors are intended to facilitate the description of the example embodiments of the present disclosure, and are not intended to limit the structure of the example embodiments of the present disclosure to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments. Terms of rough approximation, such as "generally," are understood by those of ordinary skill to refer to a characteristic or feature of that bears resemblance to something, such that it is reasonable to draw a comparison to facilitate understanding, without requiring that the characteristic or feature be exactly the same, or even substantially the same, as the thing to which it is compared.

Although example embodiments have been shown and described, it should be apparent that many variations and alternate embodiments could be implemented in accordance with the present disclosure. It is understood, therefore, that the invention is not to be limited except in accordance with the appended claims and equivalents thereof.

What is claimed is:

1. A handheld portable oxygen monitor for monitoring oxygen in a weld zone, comprising:
    an oxygen monitor housing having a front, a back, a top, a bottom, and two sides extending between the front and back and the top and bottom;
    the housing having a hand-holding portion that is sized and configured to be held in the palm of a hand of a monitor user, with the user's thumb engaging one of the two sides and the user's remaining fingers engaging the other of the two sides;
    a user interface on the front of the housing, the user interface including an oxygen monitor display and one or more user interface buttons;
    a gas inlet port on the housing configured to receive a gas;
    one or more oxygen sensors within the housing operate to receive the gas from the gas inlet port, detect oxygen in the gas, and generate oxygen sensor outputs indicative of oxygen levels in the gas;
    a pump within the housing having a pump inlet in fluid communication with the gas inlet port and a pump outlet in fluid communication with the one or more oxygen sensors;
    the oxygen monitor being characterized by one or more improvements selected from the group consisting of:
    (1) a replaceable dust filter element removably disposed in a gas inlet pathway within the housing extending from the gas inlet port to the one or more oxygen sensors, the replaceable dust filter element being formed as a sintered metal disk and being removably seated in a filter receptacle of corresponding size and shape that forms part of the gas inlet pathway, the filter receptacle being formed as part of the housing and covered by a removable cover of the housing having an interior surface formed with a tubular socket that receives the filter receptacle when the removable cover is secured as part of the housing, the gas inlet port being disposed on the removable cover and forming part of a closed gas pathway that includes the tubular socket in receiving engagement with the filter receptacle having the replaceable dust filter element disposed therein;
    (2) a modular sensor system comprising an oxygen sensor module that includes the one or more oxygen sensors and a sensor module circuit board on which the one or more oxygen sensors are mounted, the sensor module circuit board including a plug-in connector providing electrical connectivity to a main circuit board of the portable handheld oxygen monitor, the oxygen sensor module being removably mounted in the housing by way of the sensor module circuit board being removably mounted to a circuit board holder, such that the oxygen sensor module is interchangeable with other oxygen sensor modules having sensor module circuit boards with a common form factor by removing the sensor module circuit board of the oxygen sensor module from the circuit board holder and inserting therein a different sensor module circuit board of one of the other oxygen sensor modules, the one or more oxygen sensors each being configured to sense oxygen within a specified oxygen sensitivity range and having dedicated gas inlet and outlet ports;
    the modular sensor system further comprising configurable internal gas pathway components within the housing, the configurable internal gas pathway components comprising dedicated gas inlet and outlet tubes connected to the dedicated gas inlet and outlet ports of the one or more oxygen sensors; and (3) an oxygen monitor communication interface, an oxygen monitor storage, and an oxygen monitor controller, the oxygen monitor controller operating to perform program operations that provide an application program interface for a remote device in communication with the oxygen monitor that enables the remote device to (a) control one or more operations of the oxygen monitor, (b) receive real-time oxygen monitoring data from the oxygen monitor for display on the remote device, (c) upload logging event data from the oxygen monitor storage, (d) retrieve static system information including one or more of unit serial number, hardware version, firmware version, manufacturing data, oxygen sensor serial number, factory calibration values, current calibration values and calibration dates, and runtime state information including one or more of status messages, fault codes, core/stack dump data and troubleshooting information generated during device operations, from the oxygen monitor storage, and (e) perform firmware updates on the oxygen monitor to modify its programming stored in a non-volatile code memory component of an oxygen monitor memory.

2. The oxygen monitor of claim 1, comprising at least two of the improvements (1)-(3).

3. The oxygen monitor of claim 1, comprising all three of the improvements (1)-(3).

4. The oxygen monitor of claim 1, wherein the replaceable dust filter element of the improvement (1) is accessible by way of the removable cover.

5. The oxygen monitor of claim 1, wherein the modular sensor system of the improvement (2) comprises the one or more oxygen sensors including one or both of a first oxygen sensor having a first oxygen sensitivity range and first dedicated gas inlet and outlet ports, or a second oxygen sensor having a second oxygen sensitivity range and second dedicated gas inlet and outlet ports.

6. The oxygen monitor of claim 5, wherein the first oxygen sensor comprises an optical oxygen sensor, and wherein the second oxygen sensor comprises a solid-electrolyte sensor.

7. The oxygen monitor of claim 5, wherein the first oxygen sensor operates to detect between approximately 209,000 ppm to 100 ppm oxygen in the gas, and the second oxygen sensor operates to detect between approximately 1000 ppm to 5 ppm oxygen in the gas.

8. The oxygen monitor of claim 5, wherein the sensor module circuit board has the first oxygen sensor but not the second oxygen sensor mounted thereto, and wherein the configurable internal gas pathway components of the improvement (2) comprise internal gas pathway components providing fluid communication from the gas inlet port on the housing to the pump and thereafter from the pump to the first oxygen sensor, the configurable internal gas pathway components comprising flexible tubing that is detachably mounted to the first oxygen sensor.

9. The oxygen monitor of claim 5, wherein the sensor module circuit board has the first oxygen sensor but not the second oxygen sensor mounted thereto, and wherein the configurable internal gas pathway components of the improvement (2) comprise a first flexible tube detachably connected between a first orifice in fluid communication with the gas inlet port on the housing and a second orifice in fluid communication with the pump inlet, a second flexible tube detachably connected between a third orifice in fluid communication with the pump outlet and a fourth orifice formed as the dedicated gas inlet port on the first oxygen sensor, and a third flexible tube detachably connected between a fifth orifice formed as the dedicated gas outlet port on the first oxygen sensor and a sixth orifice in fluid communication with a gas outlet on the housing.

10. The oxygen monitor of claim 5, wherein the sensor module circuit board has both of the first and second oxygen sensors mounted thereto, and wherein the configurable internal gas pathway components of the improvement (2) comprise configurable internal gas pathway components providing fluid communication from the gas inlet port on the housing to the pump, and thereafter from the pump to the first oxygen sensor, and thereafter from the first oxygen sensor to the second oxygen sensor, the configurable internal gas pathway components comprising flexible tubing that is detachably mounted to the first and second oxygen sensors.

11. The oxygen monitor of claim 5, wherein the sensor module circuit board has both of the first and second oxygen sensors mounted thereto, and wherein the configurable internal gas pathway components of the improvement (2) comprise a first flexible tube detachably connected between a first orifice in fluid communication with the gas inlet port on the housing and a second orifice in fluid communication with the pump inlet, a second flexible tube detachably connected between a third orifice in fluid communication with the pump outlet and a fourth orifice formed as the dedicated gas inlet port on the first oxygen sensor, a third flexible tube detachably connected between a fifth orifice formed as the dedicated gas outlet port on the first oxygen sensor and a sixth orifice formed as the dedicated gas inlet port on the second oxygen sensor, and a fourth flexible tube detachably connected between a seventh orifice formed as the dedicated gas outlet port on the second oxygen sensor and an eighth orifice in fluid communication with a gas outlet on the housing.

12. The oxygen monitor of claim 1, wherein the oxygen monitor program operations of the improvement (3) include the application program interface further being to enable the remote device to reset current calibration settings of the oxygen monitor to factory calibration settings.

13. A handheld portable oxygen monitor for monitoring oxygen in a weld zone, comprising:
- an oxygen monitor housing having a front, a back, a top, a bottom, and two sides extending between the front and back and the top and bottom;
- the housing having a hand-holding portion that is sized and configured to be held in the palm of a hand of a monitor user, with the user's thumb engaging one of the two sides and the user's remaining fingers engaging the other of the two sides;
- a user interface on the front of the housing, the user interface including an oxygen monitor display and one or more user interface buttons;
- a gas inlet port on the housing configured to receive a gas;
- one or more oxygen sensors within the housing operate to receive the gas from the gas inlet port, detect oxygen in the gas, and generate oxygen sensor outputs indicative of oxygen levels in the gas;
- a pump within the housing having a pump inlet in fluid communication with the gas inlet port and a pump outlet in fluid communication with the one or more oxygen sensors; and
- a replaceable dust filter element removably disposed in a gas inlet pathway within the housing extending from the gas inlet port to the one or more oxygen sensors, the replaceable dust filter element being formed as a sintered metal disk and being removably seated in a filter receptacle of corresponding size and shape that forms part of the gas inlet pathway, the filter receptacle being formed as part of the housing and covered by a removable cover of the housing having an interior surface formed with a tubular socket that receives the filter receptacle when the removable cover is secured as part of the housing, the gas inlet port being disposed on the removable cover and forming part of a closed gas pathway that includes the tubular socket in receiving engagement with the filter receptacle having the replaceable dust filter element disposed therein.

14. A handheld portable oxygen monitor for monitoring oxygen in a weld zone, comprising:
   an oxygen monitor housing having a front, a back, a top, a bottom, and two sides extending between the front and back and the top and bottom;
   the housing having a hand-holding portion that is sized and configured to be held in the palm of a hand of a monitor user, with the user's thumb engaging one of the two sides and the user's remaining fingers engaging the other of the two sides; and
   a user interface on the front of the housing, the user interface including an oxygen monitor display and one or more user interface buttons;
   a gas inlet port on the housing configured to receive a gas;
   one or more oxygen sensors within the housing operate to receive the gas from the gas inlet port, detect oxygen in the gas, and generate oxygen sensor outputs indicative of oxygen levels in the gas;
   a pump within the housing having a pump inlet in fluid communication with the gas inlet port and a pump outlet in fluid communication with the one or more oxygen sensors;
   a replaceable dust filter element removably disposed in a gas inlet pathway within the housing extending from the gas inlet port to the one or more oxygen sensors; and
   a modular sensor system comprising an oxygen sensor module that includes the one or more oxygen sensors and a sensor module circuit board on which the one or more oxygen sensors are mounted, the sensor module circuit board including a plug-in connector providing electrical connectivity to a main circuit board of the portable handheld oxygen monitor, the oxygen sensor module being removably mounted in the housing by way of the sensor module circuit board being removably mounted to a circuit board holder, such that the oxygen sensor module is interchangeable with other oxygen sensor modules having sensor module circuit boards with a common form factor by removing the sensor module circuit board of the oxygen sensor module from the circuit board holder and inserting therein a different sensor module circuit board of one of the other oxygen sensor modules, the one or more oxygen sensors each being configured to sense oxygen within a specified oxygen sensitivity range and having dedicated gas inlet and outlet ports.

15. A handheld portable oxygen monitor for monitoring oxygen in a weld zone, comprising:
   an oxygen monitor housing having a front, a back, a top, a bottom, and two sides extending between the front and back and the top and bottom;
   the housing having a hand-holding portion that is sized and configured to be held in the palm of a hand of a monitor user, with the user's thumb engaging one of the two sides and the user's remaining fingers engaging the other of the two sides; and
   a user interface on the front of the housing, the user interface including an oxygen monitor display and one or more user interface buttons;
   a gas inlet port on the housing configured to receive a gas;
   one or more oxygen sensors within the housing operate to receive the gas from the gas inlet port, detect oxygen in the gas, and generate oxygen sensor outputs indicative of oxygen levels in the gas;
   a pump within the housing having a pump inlet in fluid communication with the gas inlet port and a pump outlet in fluid communication with the one or more oxygen sensors;
   a replaceable dust filter element removably disposed in a gas inlet pathway within the housing extending from the gas inlet port to the one or more oxygen sensors;
   a modular sensor system comprising an oxygen sensor module that includes the one or more oxygen sensors and a sensor module circuit board on which the one or more oxygen sensors are mounted, the sensor module circuit board including a plug-in connector providing electrical connectivity to a main circuit board of the portable handheld oxygen monitor, the oxygen sensor module being removably mounted in the housing by way of the sensor module circuit board being removably mounted to a circuit board holder, such that the oxygen sensor module is interchangeable with other oxygen sensor modules having sensor module circuit boards with a common form factor by removing the sensor module circuit board of the oxygen sensor module from the circuit board holder and inserting therein a different sensor module circuit board of one of the other oxygen sensor modules, the one or more oxygen sensors each being configured to sense oxygen within a specified oxygen sensitivity range and having dedicated gas inlet and outlet ports; and
   configurable internal gas pathway components within the housing, the configurable internal gas pathway components comprising dedicated gas inlet and outlet tubes connected to the dedicated gas inlet and outlet ports of the one or more oxygen sensors.

16. A handheld portable oxygen monitor for monitoring oxygen in a weld zone, comprising:
   an oxygen monitor housing having a front, a back, a top, a bottom, and two sides extending between the front and back and the top and bottom;
   the housing having a hand-holding portion that is sized and configured to be held in the palm of a hand of a monitor user, with the user's thumb engaging one of the two sides and the user's remaining fingers engaging the other of the two sides; and
   a user interface on the front of the housing, the user interface including an oxygen monitor display and one or more user interface buttons;
   a gas inlet port on the housing configured to receive a gas;
   one or more oxygen sensors within the housing operate to receive the gas from the gas inlet port, detect oxygen in the gas, and generate oxygen sensor outputs indicative of oxygen levels in the gas;
   a pump within the housing having a pump inlet in fluid communication with the gas inlet port and a pump outlet in fluid communication with the one or more oxygen sensors;
   a replaceable dust filter element removably disposed in a gas inlet pathway within the housing extending from the gas inlet port to the one or more oxygen sensors;

a modular sensor system comprising an oxygen sensor module that includes the one or more oxygen sensors and a sensor module circuit board on which the one or more oxygen sensors are mounted, the sensor module circuit board being removably mounted to a circuit board holder such that the oxygen sensor module is interchangeable with other oxygen sensor modules having a common form factor;

configurable gas pathway components within the housing;

an oxygen monitor communication interface;

an oxygen monitor storage;

an oxygen monitor controller in electrical communication with the oxygen monitor communication interface and the storage; and the oxygen monitor controller operating to perform program operations that provide an application program interface for a remote device in communication with the oxygen monitor that enables the remote device to (a) control one or more operations of the oxygen monitor, (b) receive real-time oxygen monitoring data from the oxygen monitor for display on the remote device, (c) upload logging event data from the oxygen monitor storage, (d) retrieve static system information including one or more of unit serial number, hardware version, firmware version, manufacturing data, oxygen sensor serial number, factory calibration values, current calibration values and calibration dates, and runtime state information including one or more of status messages, fault codes, core/stack dump data and troubleshooting information generated during device operations, from the oxygen monitor storage, and (e) perform firmware updates on the oxygen monitor to modify its programming stored in a non-volatile code memory component of an oxygen monitor memory.

17. A combination of the oxygen monitor of claim 16 and a remote device, the remote device communicating with the oxygen monitor and accessing the oxygen monitor's application program interface for the remote device to (a) control the one or more operations of the oxygen monitor, (b) receive and display the real-time oxygen monitoring data from the oxygen monitor, (c) upload the logging event data from the oxygen monitor storage, (d) retrieve the oxygen monitor's static system information including the one or more of unit serial number, hardware version, firmware version, manufacturing data, oxygen sensor serial number, factory calibration values, current calibration values and calibration dates, and the oxygen monitor's runtime state information including the one or more of status messages, fault codes, core/stack dump data and troubleshooting information generated during device operations, from the oxygen monitor storage, and (e) perform the firmware updates on the oxygen monitor to modify its programming stored in the non-volatile code memory component of the oxygen monitor memory.

18. The combination of claim 17, wherein the remote device communicates the oxygen monitor's static system information and runtime state information obtained from the oxygen monitor to remote analytical equipment for manufacturer analysis and troubleshooting of oxygen monitor operations by the remote analytical equipment, whereby the remote device acts as a service agent proxy for the remote analytical equipment to access the oxygen monitor and retrieve and forward the oxygen monitor's static system information and runtime state information for remote analysis.

* * * * *